US012745911B2

(12) United States Patent
Kim

(10) Patent No.: US 12,745,911 B2
(45) Date of Patent: Sep. 29, 2026

(54) ORAL IMAGE PROCESSING DEVICE AND ORAL IMAGE PROCESSING METHOD

(71) Applicant: MEDIT CORP., Seoul (KR)

(72) Inventor: Dusu Kim, Seoul (KR)

(73) Assignee: MEDIT CORP., Seoul (KR)

( * ) Notice: Subject to any disclaimer, the term of this patent is extended or adjusted under 35 U.S.C. 154(b) by 125 days.

(21) Appl. No.: 18/700,878

(22) PCT Filed: Oct. 17, 2022

(86) PCT No.: PCT/KR2022/015748

§ 371 (c)(1),
(2) Date: Apr. 12, 2024

(87) PCT Pub. No.: WO2023/063805

PCT Pub. Date: Apr. 20, 2023

(65) Prior Publication Data

US 2024/0398236 A1 Dec. 5, 2024

(30) Foreign Application Priority Data

Oct. 15, 2021 (KR) ........................ 10-2021-0137838

(51) Int. Cl.
*A61B 5/00* (2006.01)
*A61C 9/00* (2006.01)
*A61C 13/34* (2006.01)

(52) U.S. Cl.
CPC .......... *A61B 5/0088* (2013.01); *A61B 5/0062* (2013.01); *A61B 5/0073* (2013.01); *A61C 9/0053* (2013.01); *A61C 13/34* (2013.01)

(58) Field of Classification Search
CPC ........... A61C 13/00; A61C 13/38; A61C 7/20; A61B 34/10
See application file for complete search history.

(56) References Cited

U.S. PATENT DOCUMENTS

| | | | | |
|---|---|---|---|---|
| 8,257,083 | B2 * | 9/2012 | Berckmans, III | A61C 8/0001 433/213 |
| 8,457,772 | B2 * | 6/2013 | Giasson | B33Y 80/00 700/98 |
| 8,651,858 | B2 * | 2/2014 | Berckmans, III | A61B 34/30 433/24 |
| 8,926,328 | B2 * | 1/2015 | Suttin | A61C 13/081 433/213 |
| 11,039,905 | B2 * | 6/2021 | Je | G06T 7/0014 |

(Continued)

FOREIGN PATENT DOCUMENTS

| | | | |
|---|---|---|---|
| JP | 2013-545511 | A | 12/2013 |
| JP | 2018-196580 | A | 12/2018 |

(Continued)

OTHER PUBLICATIONS

International Search Report for PCT/KR2022/015748, dated Dec. 30, 2022.

*Primary Examiner* — Ralph A Lewis
(74) *Attorney, Agent, or Firm* — Sughrue Mion, PLLC

(57) ABSTRACT

Provided are an intraoral image processing device and an intraoral image processing method. The intraoral image processing method includes obtaining scan data regarding an object, determining a die insertion direction based on the scan data of the object, and obtaining a die model set in the die insertion direction.

13 Claims, 18 Drawing Sheets

(56) References Cited

U.S. PATENT DOCUMENTS

| | | | | |
|---|---|---|---|---|
| 2005/0019732 | A1* | 1/2005 | Kaufmann | G06T 7/12<br>433/213 |
| 2012/0270179 | A1 | 10/2012 | Holmstrom et al. | |
| 2013/0289950 | A1* | 10/2013 | Kopelman | A61C 13/0004<br>703/1 |
| 2017/0027673 | A1 | 2/2017 | Beom et al. | |
| 2020/0170755 | A1 | 6/2020 | Kumamoto et al. | |
| 2020/0383759 | A1 | 12/2020 | Je et al. | |
| 2021/0282897 | A1* | 9/2021 | Laaker | A61C 5/70 |
| 2024/0398236 | A1* | 12/2024 | Kim | B33Y 80/00 |

FOREIGN PATENT DOCUMENTS

| | | | |
|---|---|---|---|
| KR | 10-1635998 | B1 | 7/2016 |
| KR | 10-1834435 | B1 | 4/2018 |
| KR | 10-1994396 | B1 | 6/2019 |

* cited by examiner $$v = \sum_{i=1}^{n} a_i \hat{v}_i, \quad \hat{v} = v/|v|$$

$$p_{cen} = \frac{1}{n}\sum_{i=1}^{n} p_i$$

CALCULATE AVERAGE OF VERTEX COORDINATES FORMING BOUNDARY POLYLINE OF EACH OF OBJECTS

CALCULATE CENTER COORDINATE OF BOUNDING BOX INCLUDING EACH OF OBJECTS $$p_{cen} = \frac{1}{L}\sum_{i=1}^{N} \ell_i m_i, L = \sum_{i=1}^{N} \ell_i$$ , m = midpoint of a segment $e_i$ CALCULATE WEIGHTED AVERAGE WITH LENGTH OF EACH OF LINE SEGMENTS FORMING BOUNDARY POLYLINE OF EACH OF OBJECTS APPLIED, AS A WEIGHT, TO CENTER COORDINATE OF EACH OF LINE SEGMENTS

ORAL IMAGE PROCESSING DEVICE AND ORAL IMAGE PROCESSING METHOD

TECHNICAL FIELD

The disclosure relates to an intraoral image processing device and an intraoral image processing method.

BACKGROUND ART

Recently, as a method of obtaining patient's intraoral information, a method of obtaining a patient's intraoral image through a three-dimensional scanner has been used. Three-dimensional scan data of objects, such as patient's teeth, gum, jaw bone, and the like, may be obtained by scanning patient's intraoral through a three-dimensional scanner, and the obtained three-dimensional scan data is used for dental treatments, orthodontic treatments, prosthetic treatments, and the like.

A three-dimensional teeth model generated through the obtained three-dimensional scan data shows a patient the progress of an orthodontic treatment, and may be used as a material for checking a portion that is difficult to observe within the patient's intraoral. The three-dimensional teeth model may include a die model according to a treatment method. The die model may refer to a three-dimensional tooth model from individually separated teeth, and the die model may be detached from or attached to a base of the three-dimensional tooth model. For example, when a prosthesis work, such as crown or laminate, is performed on a preparation tooth, a die model reflecting the shape of the preparation tooth is detached from or attached to a three-dimensional teeth model, thereby checking whether a prosthesis fits well. Furthermore, for example, when a die model reflecting the shape of an adjacent tooth located next to a preparation tooth is generated, it may be checked whether the prostheses for the preparation tooth and the adjacent tooth are in contact with each other.

A die model may be formed by cutting a plaster model. However, as a manually-cut die model is not precise and has low user convenience, a new method to form a die model is demanded.

DISCLOSURE

Technical Problem

Embodiments are directed to provide an intraoral image processing device and an intraoral image processing method, which are capable of obtaining a three-dimensional die model by using scan data and calculating a direction in which the three-dimensional die model is formed.

Technical Solution

An intraoral image processing method according to an embodiment includes obtaining scan data regarding an object, determining a die insertion direction based on the scan data of the object, and obtaining a die model set in the die insertion direction.

An intraoral image processing device according to an embodiment includes a display, a memory to store one or more instructions, and a processor, wherein the processor is configured to, by executing the one or more instructions stored in the memory, obtain scan data regarding an object, determine a die insertion direction based on the scan data of the object, and obtain a die model set in the die insertion direction.

Advantageous Effects

According to an intraoral image processing device and an intraoral image processing method, according to the embodiments, a three-dimensional die model may be obtained by using scan data, and a direction in which the three-dimensional die model is formed may be automatically calculated.

MODE FOR INVENTION

Figure 1:
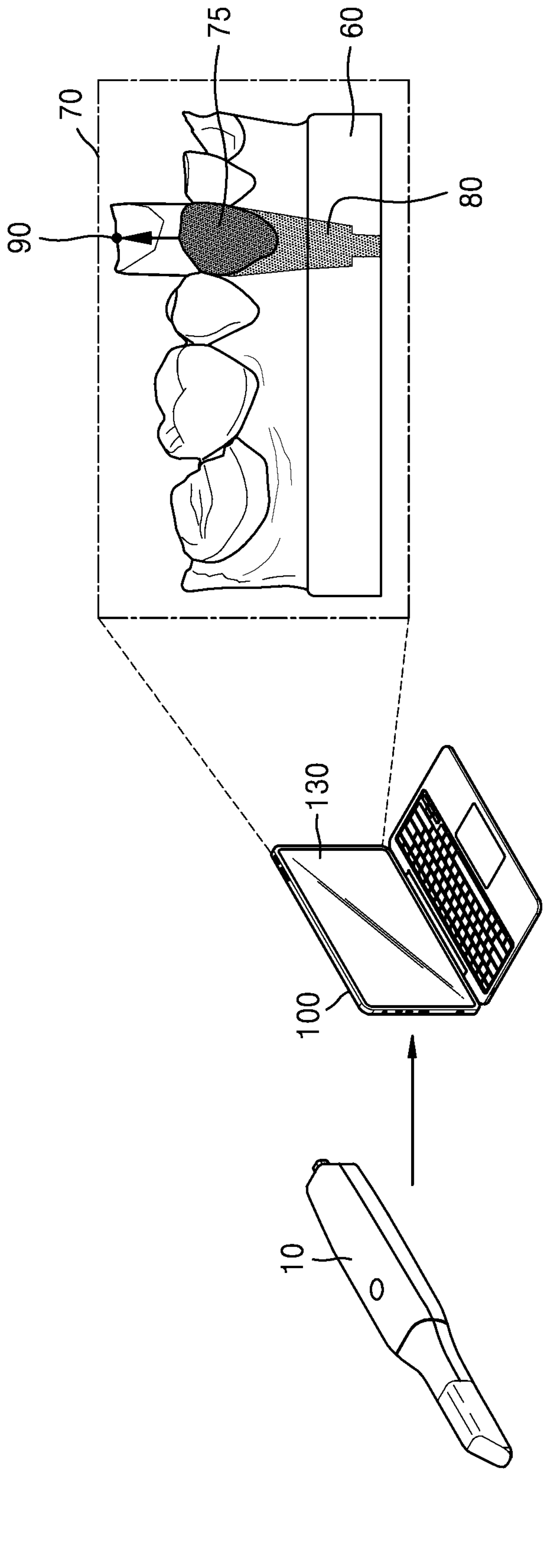
FIG. 1 is a view for explaining an intraoral image processing system according to an embodiment.

The present specification describes the principle of the disclosure and discloses embodiments to clarify the scope of rights of the disclosure and enable one skilled in the art to which the disclosure pertains to work the disclosure. The embodiments may be implemented in various forms.

Like reference numerals refer to like elements throughout the specification. This specification does not describe all elements of the embodiments, and general content in the technical field to which the inventive concept pertains or content that overlaps among the embodiments is omitted. As used herein, the term "part" or "portion" may be implemented in software or hardware, and according to embodiments, a plurality of "units" may be implemented as one unit or element, or one "unit" may include a plurality of elements. Hereinafter, the working principle and embodiments of the inventive concept will be described with reference to the accompanying drawings.

In the present specification, the image may include at least one tooth or an image representing an intraoral including at least one tooth (hereinafter, "intraoral image").

Also, in the present specification, an image may be a two-dimensional image of an object or a three-dimensional model or three-dimensional image representing the object three-dimensionally. Also, in the present specification, an image may refer to data necessary to represent an object in two or three dimensions, for example, raw data obtained from at least one image sensor. In particular, raw data is data obtained to generate an intraoral image and may be data (e.g., two-dimensional data) obtained from at least one image sensor included in an intraoral scanner when scanning the intraoral of a patient, which is an object, using the intraoral scanner.

In the present specification, an "object" may include teeth, gingiva, at least a partial region of an intraoral, and/or artificial structures (e.g., orthodontic appliances, implants, artificial teeth, orthodontic aid tools inserted into the mouth, etc.) that may be inserted into the intraoral. Here, orthodontic appliances may include at least one of brackets, attachments, orthodontic screw, lingual orthodontic appliances, and removable orthodontic retainers.

In the specification, the "three-dimensional intraoral image" may be composed of various polygonal meshes. For example, when two-dimensional data is obtained by using a three-dimensional scanner, an intraoral image processing device may calculate coordinates of a plurality of illuminated surface points using a triangulation method. As the amount of scan data increases by scanning the surface of the object while moving by using the three-dimensional scanner, the coordinates of the surface points may be accumulated. As a result of this image acquisition, a point cloud of vertices may be identified to represent the extent of the surface. Points in the point cloud may represent actual measured points on the three-dimensional surface of the object. The surface structure may be approximated by forming a polygonal mesh in which adjacent vertices of a point cloud are connected by line segments. The polygonal mesh may be variously determined, such as a triangular, quadrangular, pentagonal mesh, or the like. The relationship between the polygons of the mesh model and the neighboring polygons may be used to extract features of a tooth boundary, for example, a curvature, a smallest curvature, an edge, a spatial relationship, and the like.

Hereinafter, embodiments will be described in detail with reference to the drawings.

FIG. 1 is a view for explaining an intraoral image processing system according to an embodiment.

Referring to FIG. 1, the intraoral image processing system may include a three-dimensional scanner 10 and an intraoral image processing device 100.

The three-dimensional scanner 10 according to an embodiment is a device that scans an object and is used as a medical device that obtains an image of an object. The three-dimensional scanner 10 may obtain an image of at least one of an intraoral, an artificial structure, or a plaster model modeled after the intraoral or the artificial structure.

Although FIG. 1 illustrates that the three-dimensional scanner 10 is in the form of a hand-held scanner held in a user's hand to scan an object, the disclosure is not limited thereto. For example, the three-dimensional scanner 10 may be a model scanner that scans a teeth model by installing and moving the teeth model and the like.

For example, the three-dimensional scanner 10 may be a device for obtaining an image of an intraoral including at least one tooth by being inserted into the intraoral to scan teeth in a non-contact manner. Furthermore, the three-dimensional scanner 10 may have a shape capable of being inserted into and drawn out from an intraoral, and scan the inside of a patient's intraoral by using at least one image sensor (e.g., an optical camera, etc.).

The three-dimensional scanner 10 may obtain object surface information as raw data to image at least one surface of a teeth and a gingiva in a target intraoral, and an artificial structure (e.g., orthodontic appliances including brackets, wires, and the like, implants, artificial teeth, orthodontic aid tools inserted into the mouth, etc.) that may be inserted into the intraoral.

The three-dimensional scanner 10 may transmit the obtained raw data to the intraoral image processing device 100 through a wired or wireless communication network. The image data obtained by the three-dimensional scanner 10 may be transmitted to the intraoral image processing device 100 connected through a wired or wireless communication network.

The intraoral image processing device 100 may include any electronic device that is connected to the three-dimensional scanner 10 through a wired or wireless communication network, receives a two-dimensional image obtained by scanning an object from the three-dimensional scanner 10, and is capable of generating, processing, displaying, and/or transmitting an image based on the received two-dimensional image.

The intraoral image processing device 100 may include a computing device, such as a smart phone, a laptop computer, a desktop computer, a personal digital assistant (PDA), a tablet personal computer (PC), and the like, but the disclosure is not limited thereto. Furthermore, the intraoral image processing device 100 may be present in the form of a server (or a server device) to process an intraoral image, and the like.

The intraoral image processing device 100 may generate information by processing the two-dimensional image data received from the three-dimensional scanner 10, or generate an image by processing the two-dimensional image data. Furthermore, the intraoral image processing device 100 may display the generated information and image through a display 130.

Furthermore, the three-dimensional scanner 10 may transmit the raw data obtained through scanning, as it is, to the intraoral image processing device 100. In this case, the intraoral image processing device 100 may generate a three-dimensional intraoral image that represents an intraoral in three dimensions, based on the received raw data. The intraoral image processing device 100 according to an embodiment may generate, based on the received raw data, three-dimensional data (e.g., surface data, mesh data, etc.) that represents the shape of a surface of an object in three dimensions.

Furthermore, as the "three-dimensional intraoral image" may be generated by modeling an object in three dimensions based on the received raw data, the three-dimensional intraoral image may be referred to as a "three-dimensional intraoral model". In the following description, a model or image that represents an object in two dimensions or three dimensions is collectively referred to as an "intraoral image."

Furthermore, the intraoral image processing device 100 may analyze, process, and display the generated intraoral image, and/or transmit the generated intraoral image to an external device.

In another example, the three-dimensional scanner 10 may obtain raw data by scanning an object, generate an image corresponding to the object by processing the obtained raw data, and transmit the image to the intraoral image processing device 100. In this case, the intraoral image processing device 100 may analyze, process, display, and/or transmit the received image.

In an embodiment, the intraoral image processing device 100 is an electronic device capable of generating and displaying an image representing an object in three dimensions, which is described below in detail.

When receiving raw data obtained by scanning an object from the three-dimensional scanner 10, the intraoral image processing device 100 according to an embodiment may process the received raw data to generate a three-dimensional intraoral image (or a three-dimensional intraoral model). For convenience of explanation, a three-dimensional intraoral image of the object generated by the intraoral image processing device 100 will be referred to as "scan data."

The intraoral image processing device 100 according to an embodiment may obtain a die model 80 corresponding to an object 75 using scan data 70. The die model 80 is a three-dimensional tooth model reflecting the shape of the object 75 based on the scan data 70, and may be inserted into the cavity of a base 60 or separated from the base 60. The intraoral image processing device 100 may automatically calculate a die insertion direction 90 in which the die model 80 is inserted into the base 60. Accordingly, the intraoral image processing device 100 according to an embodiment may obtain the die model 80 that is formed in the die insertion direction 90 that is automatically calculated, and is individually separable.

Figure 2:
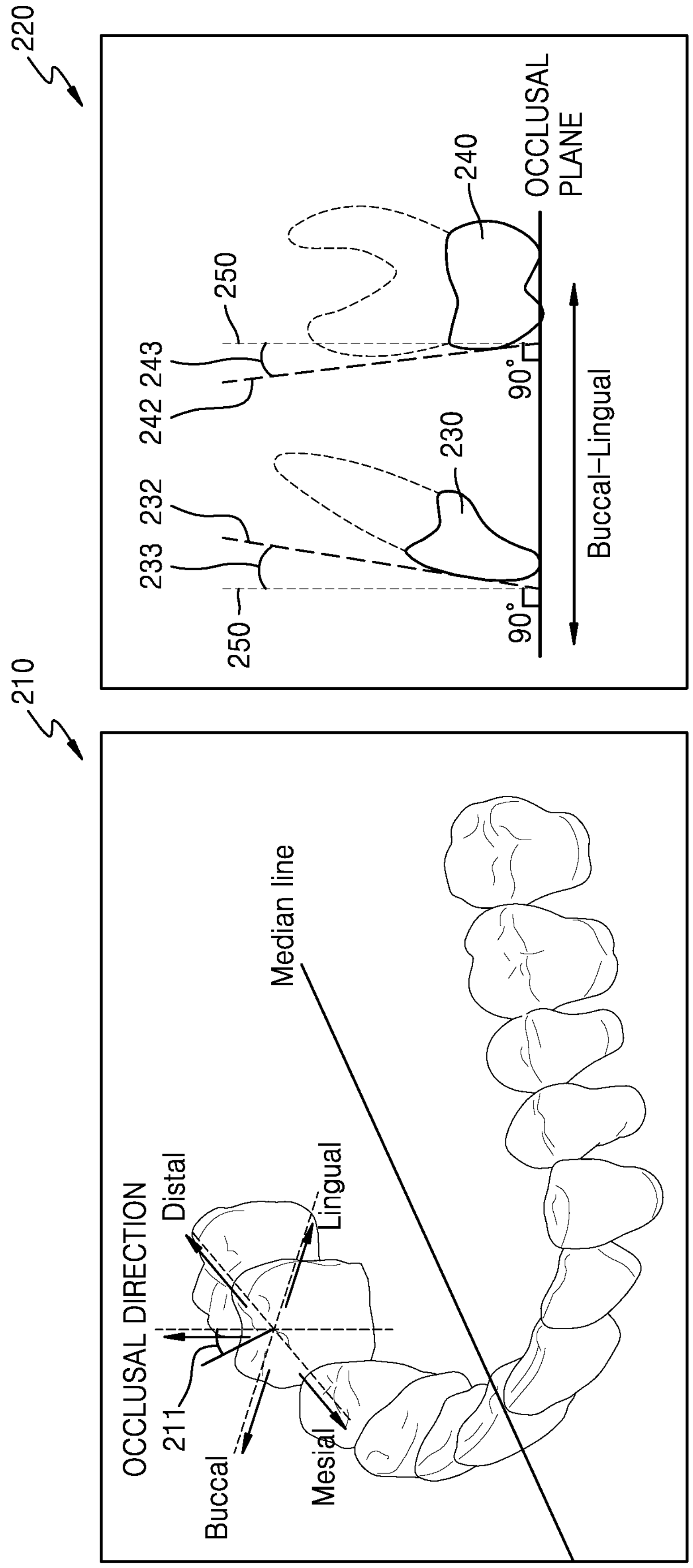
FIG. 2 is a view for explaining a direction and a threshold inclination of a tooth, according to an embodiment.

FIG. 2 is a view for explaining the direction and the threshold inclination of a tooth in a three-dimensional intraoral image according to an embodiment.

In a diagram 210 of FIG. 2, a three-dimensional intraoral image including an object arranged on an occlusal plane is illustrated.

In the diagram 210 of FIG. 2, an occlusal direction refers to an occlusal surface direction in which upper and lower jaws of teeth are engaged with each other, and the occlusal plane refers to a virtual plane formed by occlusal surfaces of teeth. In each tooth, a buccal direction may denote a direction adjacent to a cheek side, a lingual direction may denote a direction adjacent to a tongue side, a distal direction may denote a direction away from a median line along a dental arch, and a mesial direction may denote a direction toward the median line along the dental arch.

Referring to the diagram 210 of FIG. 2, each tooth may be inclined with a different tooth inclination 211 with respect to the occlusal direction. For example, a tooth may be inclined in a distal-mesial direction (e.g., a left-right direction) with respect to an occlusal direction axis or inclined buccal-lingual direction (e.g., a front-rear direction) with respect to the occlusal direction axis. The tooth inclination 211 may refer to an angle at which a long axis (or a tooth axis) of a tooth is inclined in at least any one direction of the distal direction, the mesial direction, the buccal direction, and the lingual direction, with respect to the occlusal direction axis.

In a diagram 220 of FIG. 2, teeth inclined in the buccal-lingual direction with respect to the occlusal direction axis are illustrated. The teeth may include anterior teeth 230 and posterior teeth 240. For example, the anterior teeth 230 may have a tooth inclination 233 between an occlusal direction axis 250 and a long axis 232 of a tooth. The posterior teeth 240 may have a tooth inclination 243 between the occlusal direction axis 250 and a long axis 242 of a tooth. In a tooth model according to an embodiment of the disclosure, the anterior teeth 230 may be inclined in the buccal direction, and the posterior teeth 240 may be relatively parallel to the occlusal direction. In this case, the tooth inclination 233 of the anterior teeth 230 may be greater than the tooth inclination 243 of the posterior teeth 240.

The intraoral image processing device 100 according to an embodiment of the disclosure may obtain a die insertion direction of a die model corresponding to an object considering the tooth inclination. For example, the intraoral image processing device 100 obtains a first inclination through a normal vector obtained from scan data, and when the first inclination is excessively inclined in at least any one of the distal direction, the mesial direction, the buccal direction, and the lingual direction with respect to the occlusal direction, the intraoral image processing device 100 may automatically correct the die insertion direction of a die model. For example, when the first inclination exceeds a threshold inclination, the intraoral image processing device 100 may correct such that the direction of a die model has the threshold inclination. For example, when the first inclination exceeds the threshold inclination, a die model formed in a direction based on the first inclination may face side surfaces of the gingiva and the base. For example, when the first inclination is corrected to be the threshold inclination, a die model formed in a direction based on the threshold inclination may not face the side surfaces of the gingiva and the base. In the disclosure, the threshold inclination may refer to the inclination of an object included in scan data, but the disclosure is not limited thereto.

For example, an object based on certain scan data is inclined within a certain degree of inclination (e.g., 15 degrees) in the buccal direction, and may not be inclined in the lingual direction. Furthermore, the object described above may not be inclined in the distal direction or the mesial direction. In other words, the threshold inclination of the tooth described above may have a certain inclination (e.g., 15 degrees) in the buccal direction, an inclination of 0 degrees in the lingual direction, an inclination of 0 degree in the distal direction, and an inclination of 0 degree in the mesial direction. For example, when the first inclination has an inclination of 5 degrees in the lingual direction, the intraoral image processing device 100 may automatically correct the inclination of the object to have an inclination of 0 degree in the lingual direction.

However, the threshold inclination is an example value for convenience of explanation, the disclosure is not limited to the value described above.

In the intraoral image processing device 100 according to an embodiment of the disclosure, when the scan data has occlusal plane information, the threshold inclination may be a value preset in the manner described above. However, when the scan data does not have occlusal plane information, the threshold inclination may be a value calculated through a virtual dental arch, which will be described below with reference to FIGS. 12 to 16.

Figure 3:
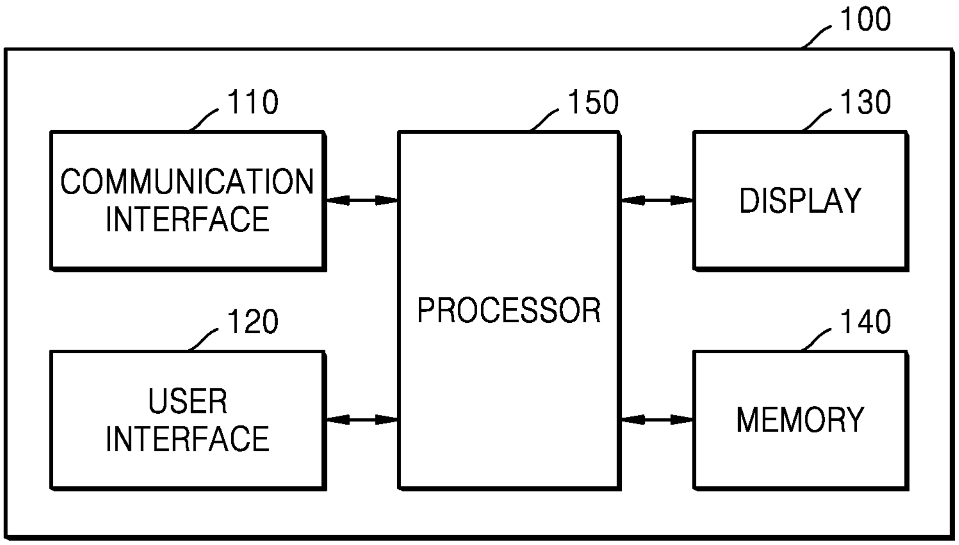
FIG. 3 is a block diagram of an intraoral image processing device according to an embodiment.

FIG. 3 is a block diagram illustrating an intraoral image processing device according to an embodiment.

Referring to FIG. 3, the intraoral image processing device 100 may include a communication interface 110, a user interface 120, the display 130, a memory 140, and a processor 150.

The communication interface 110 may communicate with at least one external electronic device (e.g., the three-dimensional scanner 10, a server, or an external medical device, etc.) through a wired or wireless communication network. The communication interface 110 may communicate with at least one external electronic device under the control of the processor 150.

In particular, the communication interface 110 may include at least one short-range communication module for performing communication according to communication standards, such as Bluetooth, Wi-Fi, Bluetooth low energy (BLE), NFC/RFID, Wi-Fi direct, UWB, or ZIGBEE.

In addition, the communication interface 110 may further include a long-range communication module that communicates with a server for supporting long-range communication according to the long-range communication standard. In particular, the communication interface 110 may include a long-range communication module for performing communication through a network for Internet communication. In addition, the communication interface 110 may include a long-range communication module for performing communication through a communication network conforming to a communication standard, such as 3G, 4G, and/or 5G.

In addition, the communication interface 110 may include at least one port for connecting to an external electronic device by a wired cable to communicate with an external electronic device (e.g., the three-dimensional scanner 10, etc.) by wire. Accordingly, the communication interface 110 may communicate with an external electronic device connected by wire through at least one port.

The user interface 120 may receive a user input for controlling the intraoral image processing device 100. The user interface 120 may include a user input device including a touch panel for sensing a user's touch, a button for receiving a user's push operation, a mouse or keyboard for designating or selecting a point on a user interface screen, and the like, but the disclosure is not limited thereto.

Also, the user interface 120 may include a voice recognition device for voice recognition. For example, the voice recognition device may be a microphone, and the voice recognition device may receive a user's voice command or voice request. Accordingly, the processor 150 may control an operation corresponding to a voice command or a voice request to be performed.

The display 130 displays a screen. In particular, the display 130 may display a certain screen under the control of the processor 150. In particular, the display 130 may display a user interface screen including an intraoral image generated based on data obtained by scanning the intraoral of a patient in the scanning apparatus 200. Alternatively, the display 130 may display a user interface screen including information related to a patient's dental treatment.

The memory 140 may store at least one instruction. Also, the memory 140 may store at least one instruction to be executed by the processor 150. Also, the memory 140 may store at least one program executed by the processor 150. In addition, the memory 140 may store data received from the three-dimensional scanner 10 (e.g., raw data obtained through intraoral scanning, etc.). Alternatively, the memory 140 may store an intraoral image representing the intraoral in three dimensions.

The processor 150 performs the at least one instruction stored in the memory 140 to control an intended operation to be performed. Here, the at least one instruction may be stored in an internal memory included in the processor 150 or in a memory 140 included in the intraoral image processing device 100 separately from the processor 150.

In particular, the processor 150 may perform at least one instruction to control at least one configuration included in the intraoral image processing device 100 so that an intended operation is performed. Therefore, even if the processor 150 performs certain operations as an example, the processor 150 may control at least one component included in the intraoral image processing device 100 so that preset operations are performed.

The processor 150 according to an embodiment may obtain, by executing the one or more instructions stored in the memory 140, scan data regarding an object. The processor 150 may determine a die insertion direction based on the scan data of the object. The processor 150 may obtain a die model set in a die insertion direction.

The processor 150 according to an embodiment may adjust, by executing the one or more instructions stored in the memory 140, a lower end of the die model to face a bottom of the base.

The processor 150 according to an embodiment may adjust, by executing the one or more instructions stored in the memory 140, the die insertion direction not to face side surfaces of the gingiva and the base.

The processor 150 according to an embodiment may adjust, by executing the one or more instructions stored in the memory 140, the die insertion direction not to be inclined in the mesial direction and the distal direction with respect to the occlusal direction.

The processor 150 according to an embodiment may obtain, by executing the one or more instructions stored in the memory 140, a first inclination of the object based on the mesh information included in the scan data of the object. The processor 150 may determine a final die insertion direction based on a result of comparing the first inclination of the object with the threshold inclination.

The processor 150 according to an embodiment may determine, by executing the one or more instructions stored in the memory 140, the threshold inclination as the final die insertion direction in response to the first inclination of the object being greater than the threshold inclination, and determine the first inclination as the final die insertion direction in response to the first inclination of the object being less than or equal to the threshold inclination.

The processor 150 according to an embodiment may obtain, by executing the one or more instructions stored in the memory 140, a weighted average normal vector with an area applied, as a weight, to a normal vector based on the mesh information included in the scan data of the object. The processor 150 may obtain the first inclination of the object based on the weighted average normal vector.

The processor 150 according to an embodiment, by executing the one or more instructions stored in the memory 140, may obtain the threshold inclination according to an angle of the object being inclined from the median line of a dental arch, based on the occlusal plane information of the scan data.

The processor 150 according to an embodiment may obtain, by executing the one or more instructions stored in the memory 140, a center point of a boundary polyline of each of objects from the scan data. The processor 150 may obtain a virtual dental arch connecting the center points of respective objects. The processor 150 may calculate the threshold inclination of each of the objects from the virtual dental arch.

The threshold inclination may include an angle of any one of the buccal direction, the lingual direction, the mesial direction, and the distal direction with respect to the occlusal direction.

The processor 150 according to an embodiment may receive a user input to select a target tooth from the scan data through the user interface 120.

The processor 150 according to an embodiment may be embodied in the form of internally including at least one internal processor and a memory device (e.g., RAM, ROM, etc.) to store at least one of a program, an instruction, a signal, and data to be processed or used in the internal processor.

Furthermore, the processor 150 may include a graphics processing unit (GPU) for processing graphics corresponding to a video. Furthermore, the processor 150 may be embodied in a system-on-chip (SoC) incorporating a core and the GPU. Furthermore, the processor 150 may include a multicore of a single core or more. For example, the processor 150 may include a dual core, a triple core, a quad core, a hexa core, an octa core, a deca core, a dodeca core, a hexadecimal core, and the like.

In an embodiment, the processor 150 may generate an intraoral image based on the two-dimensional image received from the three-dimensional scanner 10.

In detail, the communication interface 110 may receive, under the control of the processor 150, data obtained from the three-dimensional scanner 10, for example, the raw data obtained through intraoral scanning. The processor 150 may generate a three-dimensional intraoral image representing an intraoral in three dimensions, based on the raw data received from the communication interface 110. For example, the three-dimensional scanner 10 may include a camera L corresponding to a left field of view and a camera R corresponding to a right field of view to restore a three-dimensional image according to an optical triangulation method. The three-dimensional scanner 10 may obtain L image data corresponding to the left field of view and R image data corresponding to the right field of view, respectively from the camera L and the camera R. Continuously, the three-dimensional scanner 10 may transmit raw data including the L image data and the R image data to the communication interface 110 of the intraoral image processing device 100.

Then, the communication interface 110 may transmit the received raw data to the processor 150, and the processor 150 may generate an intraoral image representing an intraoral in three dimensions based on the received raw data.

Furthermore, the processor 150 may receive, by controlling the communication interface 110, an intraoral image representing an intraoral in three dimensions directly from an external server, a medical device, and the like. In this case, the processor 150 may obtain a three-dimensional intraoral image without generating a three-dimensional intraoral image based on the raw data.

According to an embodiment, the fact that the processor 150 performs an operation of "extracting," "obtaining," "generating," and the like may include not only that the processor 150 directly performs, by executing at least one instruction, the operations described above, but also that the processor 150 controls other components to allow the operations described above to be performed.

To realize the embodiments disclosed in the disclosure, the intraoral image processing device 100 may include only some of the components illustrated in FIG. 3, or more components in addition to the components of FIG. 3.

Furthermore, the intraoral image processing device 100 may store and execute dedicated software in conjunction with the three-dimensional scanner 10. The dedicated software may be referred to as a dedicated program, a dedicated tool, or a dedicated application. When the intraoral image processing device 100 operates in conjunction with the three-dimensional scanner 10, the dedicated software stored in the intraoral image processing device 100 may be connected to the three-dimensional scanner 10 and may receive in real time data obtained through intraoral scanning. For example, a product "i500" that is a Medit's three-dimensional scanner includes dedicated software for processing data obtained through intraoral scanning. In detail, Medit has manufactured and distributed "Medit Link" that is software for processing, managing, using, and/or transmitting data obtained from a three-dimensional scanner (e.g., "i500"). The "dedicated software" refers to a program, tool, or application that is operable in conjunction with a three-dimensional scanner and various three-dimensional scanners developed and sold by various manufacturers may be commonly used. Furthermore, the dedicated software described above may be manufactured and distributed separate from a three-dimensional scanner that performs intraoral scanning.

The intraoral image processing device 100 may store and execute dedicated software corresponding to the product "i500". Transmission software may perform at least one of operations to obtain, process, store, and/or transmit an intraoral image. The dedicated software may be stored in a processor. Furthermore, the dedicated software may provide a user interface screen for using the data obtained from a three-dimensional scanner. The user interface screen provided by the dedicated software may include an intraoral image generated according to an embodiment.

Figure 4:
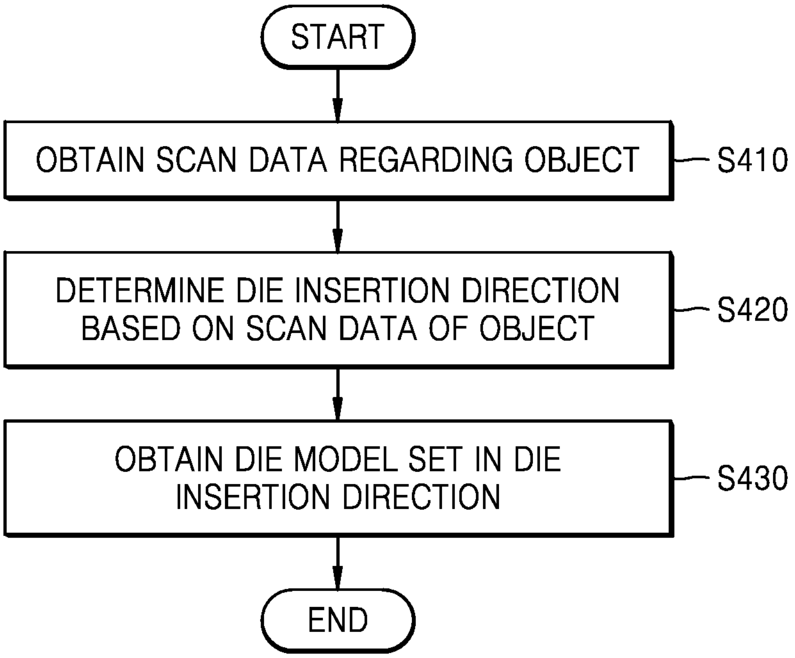
FIG. 4 is a flowchart of a method of obtaining a die model in an intraoral image processing device according to an embodiment.

FIG. 4 is a flowchart of a method of obtaining a die model in an intraoral image processing device, according to an embodiment.

The intraoral image processing method illustrated in FIG. 4 may be performed through the intraoral image processing device 100. Accordingly, the intraoral image processing method illustrated in FIG. 4 may be a flowchart showing the operations of the intraoral image processing device 100.

Referring to FIG. 4, in operation S410, the intraoral image processing device 100 may obtain scan data regarding an object.

The intraoral image processing device 100 may receive, from the three-dimensional scanner 10, raw data obtained by scanning the inside of a patient's intraoral or a teeth model, and process the received raw data, thereby obtaining the scan data regarding the object. The intraoral image processing device 100 may display scan data on the display 130.

The intraoral image processing device 100 may select, through the user interface 120, an object to obtain a die model. For example, the intraoral image processing device 100 may receive a user input to select an object through the user interface 120, and determine an object based on the received user input, which is described in FIG. 5.

In operation S420, the intraoral image processing device 100 may determine a die insertion direction based on the scan data of an object.

For example, the intraoral image processing device 100 may adjust a die insertion direction to allow a lower end of the die model to face a bottom of the base. For example, the intraoral image processing device 100 may adjust the die insertion direction not to face the side surfaces of the gingiva and the base. For example, the intraoral image processing device 100 may adjust the die insertion direction not to be inclined in the mesial direction and the distal direction with respect to the occlusal direction.

For example, the intraoral image processing device 100 may obtain the first inclination of the object based on the mesh information included in the scan data of the object. The intraoral image processing device 100 may determine a final die insertion direction based on a result of comparing the first inclination of the object with the threshold inclination. For example, when the first inclination of the object is greater than the threshold inclination, the threshold inclination may be determined to be the final die insertion direction, and when the first inclination of the object is less than or equal to the threshold inclination, the first inclination may be determined to be the final die insertion direction.

In operation S430, the intraoral image processing device 100 may obtain a die model set in a die insertion direction.

For example, the intraoral image processing device 100 may obtain a die model with a lower end facing the bottom of the base. For example, the intraoral image processing device 100 may obtain a die model in which the die insertion direction does not face the side surfaces of the gingiva and the base. For example, the intraoral image processing device 100 may obtain a die model in which the die insertion direction is not inclined in the mesial direction and the distal direction with respect to the occlusal direction.

For example, the intraoral image processing device 100 may obtain a die model formed in a direction based on an inclination that is less than or equal to the threshold inclination. For example, the intraoral image processing device 100 may obtain a die model formed in a direction based on the first inclination based on the area of a normal vector of an object, or a die model formed in a direction based on the threshold inclination. Accordingly, the die model may be prevented from being excessively inclined in buccal direction, lingual direction, mesial direction, or the distal direction according to the shape of a tooth.

The intraoral image processing method described above is described below with reference to FIGS. 5 to 7.

Figure 5:
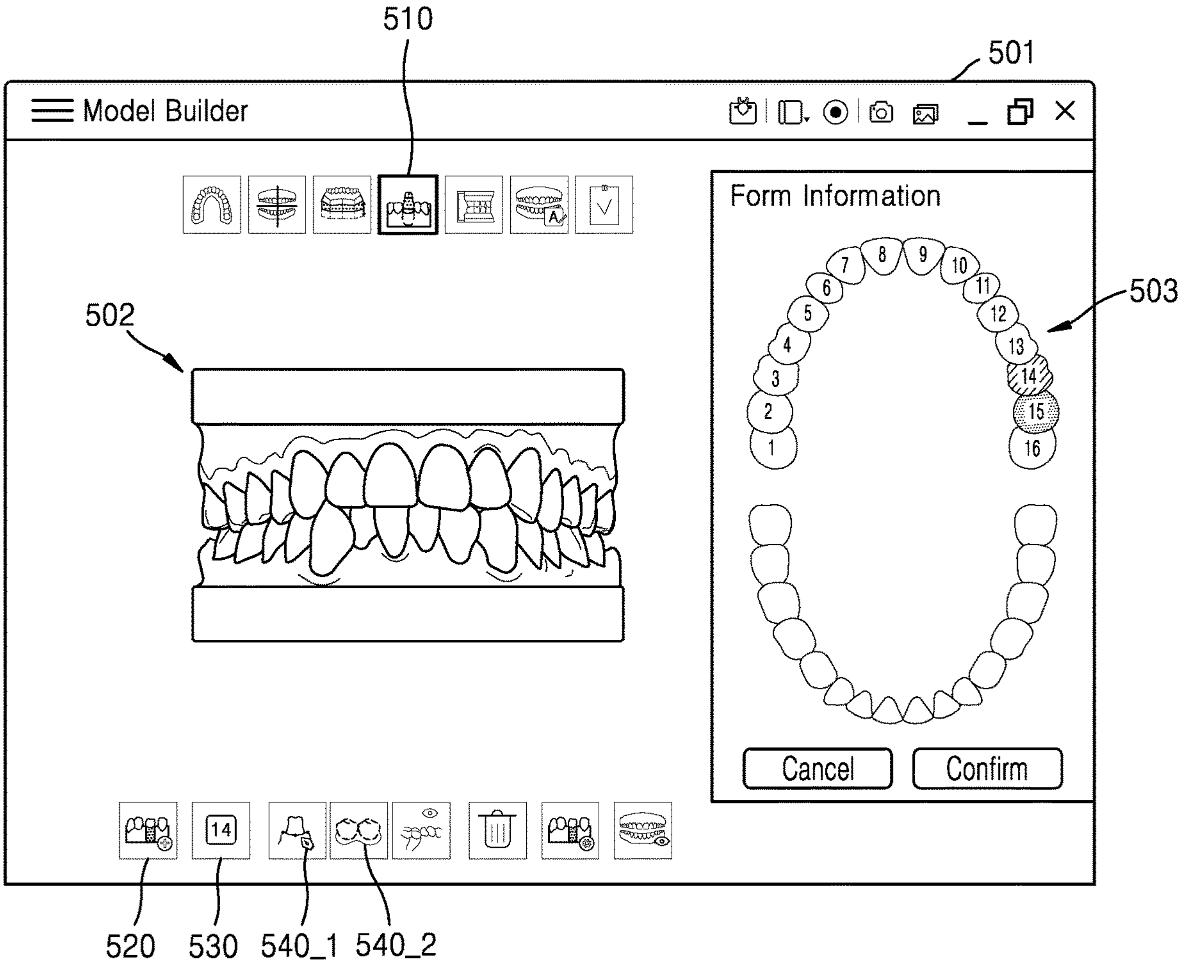
FIGS. 5, 6, and 7 are views showing an operation in which an intraoral image processing device according to an embodiment obtains a die model from scan data.
Figure 6:
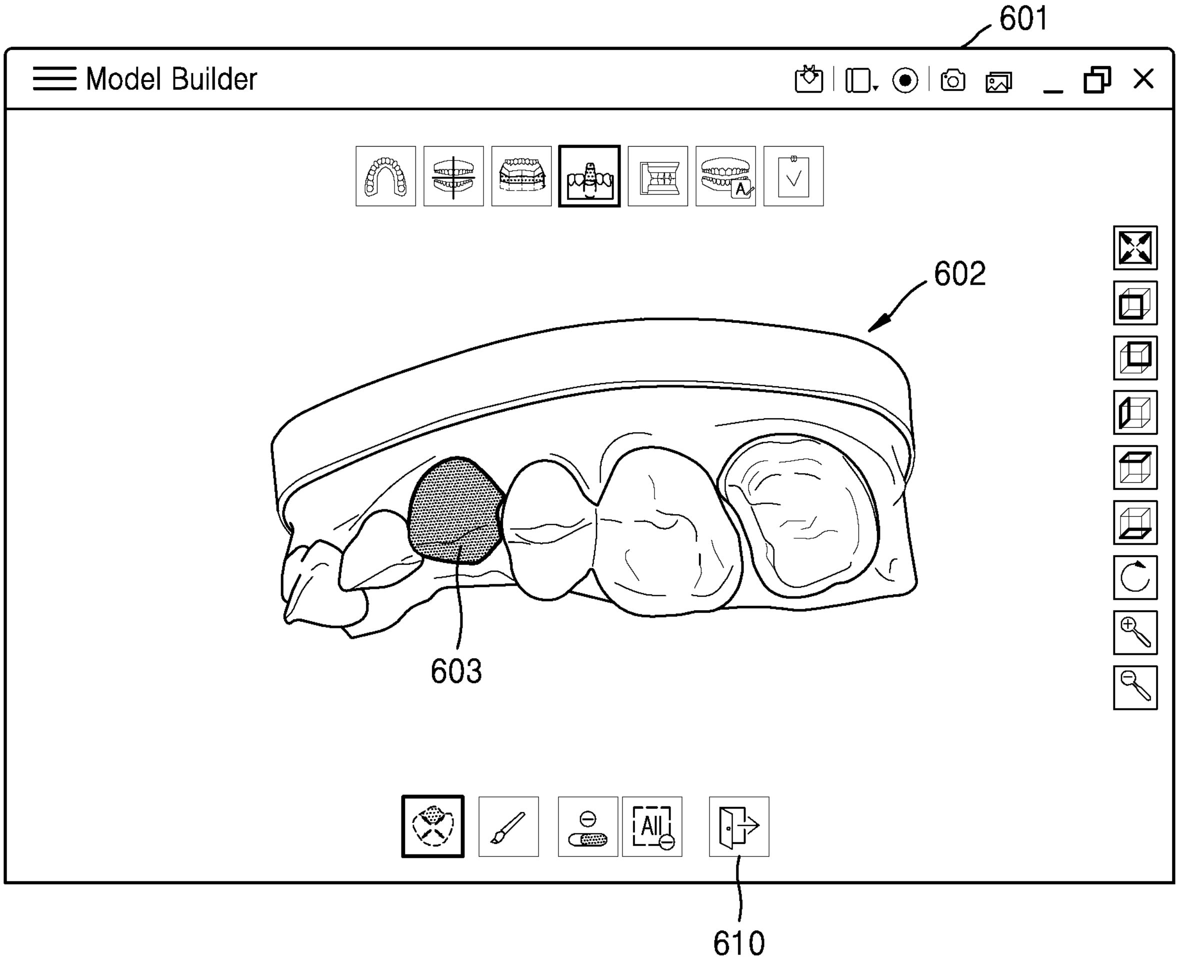
Figure 7:
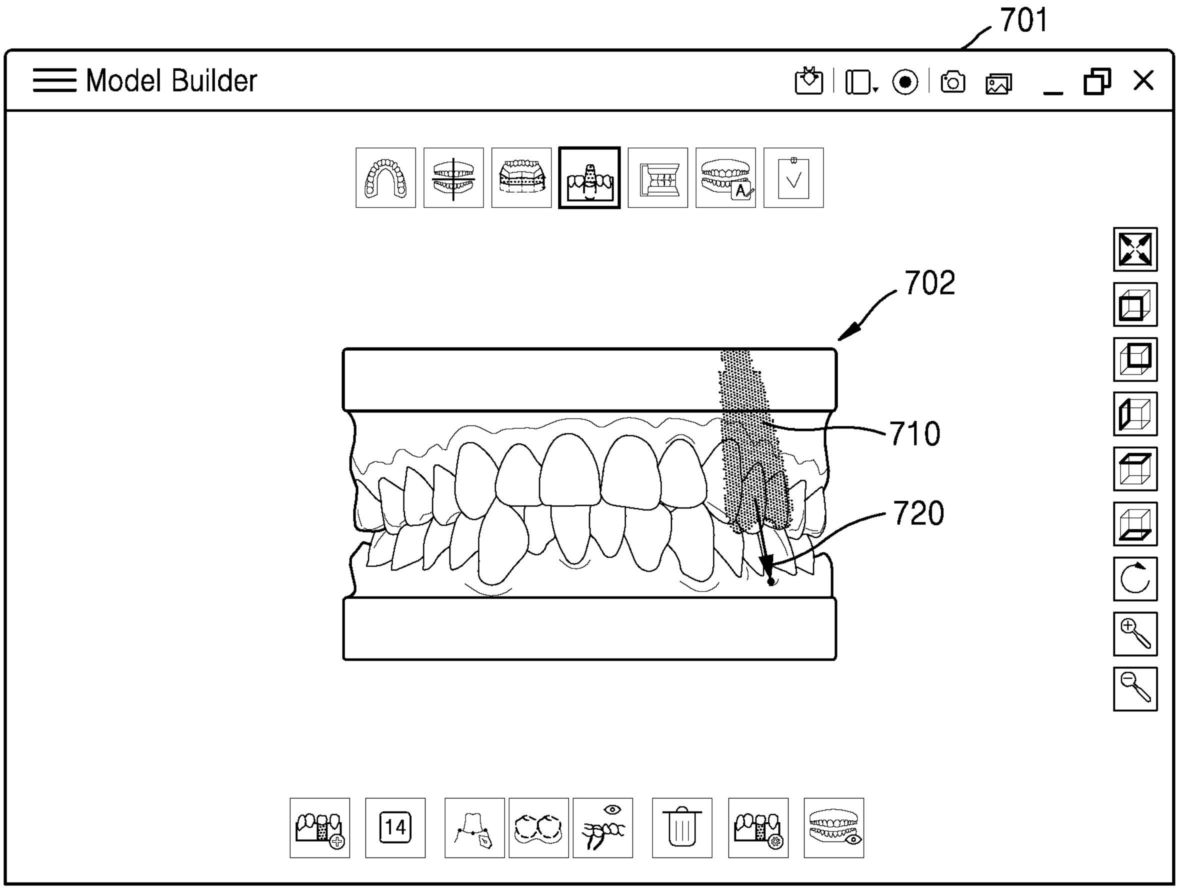

FIGS. 5, 6, and 7 are views showing an operation of obtaining, by an intraoral image processing device, a die model from scan data, according to an embodiment.

Referring to FIG. 5, the intraoral image processing device 100 according to an embodiment may generate scan data based on the raw data obtained by the three-dimensional scanner 10. Furthermore, the intraoral image processing device 100 may visually display scan data 502 through a user interface screen 501. The user interface screen 501 may be a screen of the display 130 of FIG. 1. The user interface screen 501 may include at least one menu for a user to analyze or process the scan data 502.

For example, the user interface screen 501 may include a die generation icon 510 to generate a die model from the scan data 502. When a user input to select the die generation icon 510 is received, the intraoral image processing device 100 may display at least one selection tool menu. The user interface screen 501 may include a die addition menu 520 and an object icon 530, as the selection tool menu. Furthermore, the user interface screen 501 may include an object selection screen 503.

For example, when a user input to select the die addition menu 520 is received, the intraoral image processing device 100 may display the object selection screen 503. When a user input to select one of first to n-th (e.g., $32^{nd}$) objects displayed on the object selection screen 503 is received, the intraoral image processing device 100 may determine an object based on the user input. The intraoral image processing device 100 may display the determined object as the object icon 530. For example, when a user input to select the $14^{th}$ object through the object selection screen 503 is received, the intraoral image processing device 100 may display the object icon 530 indicating that the $14^{th}$ object is determined.

Furthermore, the user interface screen 501 may include, as the selection tool menu, a tooth area menu 540 (540_1 and 540_2) to obtain a tooth area of the object. The tooth area menu 540 may include, for example, a margin line generation icon 540_1, an area selection icon 540_2, or the like. For example, when a user input to select the area selection icon 540_2 is received, the intraoral image processing device 100 may display a user interface screen 601 as shown in FIG. 6.

Referring to FIG. 6, the intraoral image processing device 100 may display the user interface screen 601 to select a tooth area from scan data 602. For example, the intraoral image processing device 100 may automatically select and display a tooth area 603 of the object based on a user input to select the object. The intraoral image processing device 100 may display the tooth area 603 including the object on the user interface screen 601. For example, the intraoral image processing device 100 may automatically obtain a tooth area of the object by employing smart selection.

In the disclosure, a method of obtaining a tooth area including an object from scan data is not limited to the embodiment described above. For example, when margin line information is already generated in scan data, the intraoral image processing device 100 may obtain a tooth area. In another example, when a user input to select the margin line generation icon 540_1 is received, the intraoral image processing device 100 may automatically identify a margin line of an object, or provide a user interface screen to select a margin line and receive a use input to set a margin line through the user interface screen. The intraoral image processing device 100 may obtain a margin line of an object based on a user input to generate a margin line, and obtain a tooth area of an object based on the margin line.

Referring back to FIG. 6, the user interface screen 601 may include an exit menu 610. The intraoral image processing device 100 may determine that the tooth area 603 of the object is obtained, based on a user input to select the exit menu 610. When the tooth area 603 of the object is determined to be obtained, the intraoral image processing device 100 may obtain a die model corresponding to the tooth area 603.

Referring to FIG. 7, the intraoral image processing device 100 may obtain inclination information of an object based on scan data 702, and obtain a die model 710 formed in a direction 720 based on the inclination information. The intraoral image processing device 100 may display, on a user interface screen 701, the die model 710 formed in the direction 720 based on the automatically calculated inclination information.

Hereinafter, a method of determining the direction of a die model based on inclination information in the intraoral image processing device 100 according to an embodiment is described with reference to FIGS. 8 to 11.

Figure 8:
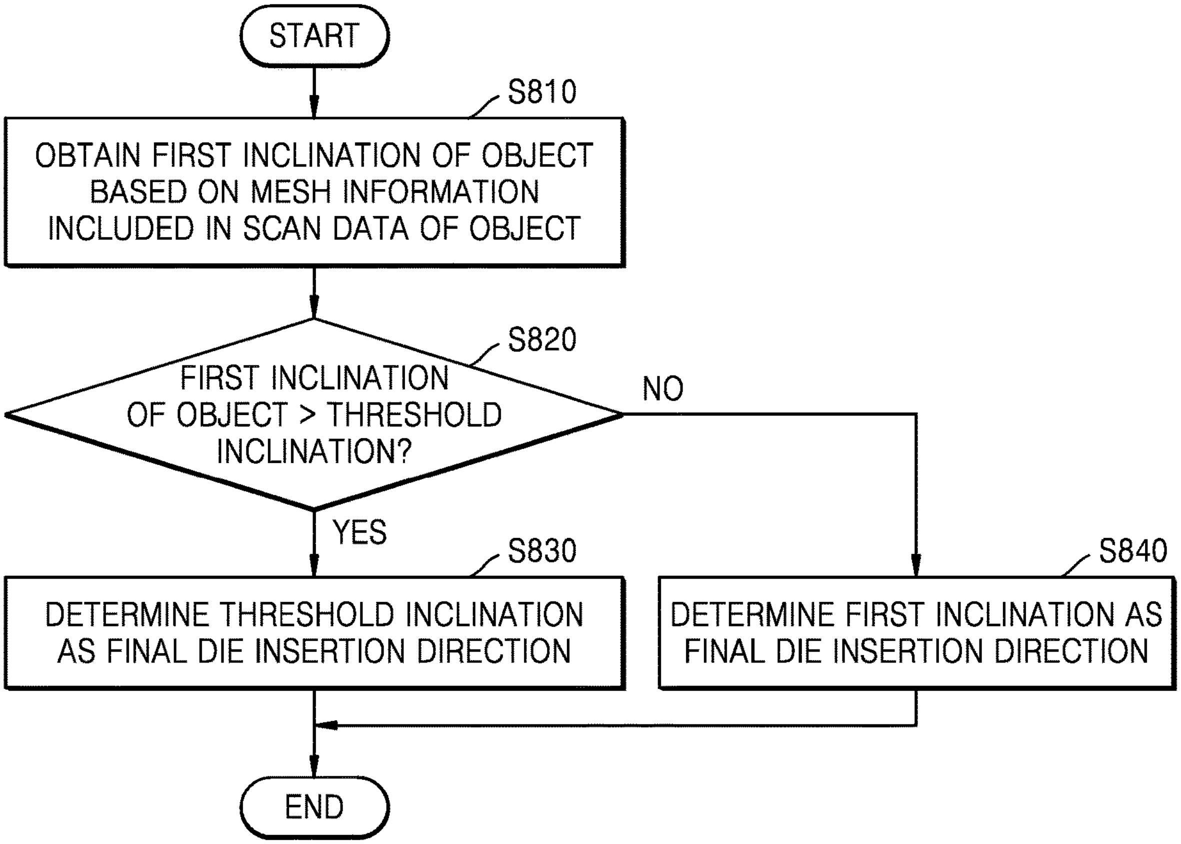
FIG. 8 is a flowchart showing a method of determining a direction of a die model in an intraoral image processing device according to an embodiment.

FIG. 8 is a flowchart showing a method of determining the direction of a die model in an intraoral image processing device according to an embodiment.

Referring to FIG. 8, in operation S810, the intraoral image processing device 100 may obtain the first inclination of the object based on the mesh information included in the scan data of the object.

For example, the scan data obtained in the intraoral image processing device 100 may be composed of various polygonal meshes. The intraoral image processing device 100 may obtain a weighted average normal vector with an area of each of meshes applied, as a weight, to a normal vector of each mesh included in the scan data of the object, and obtain a first inclination based on the weighted average normal vector. In the disclosure, the normal vector refers to a unit normal vector. In the disclosure, the weighted average normal vector refers to the average over area normal vectors obtained by applying a weight of area to each of the normal vectors. For example, the intraoral image processing device 100 may obtain the first inclination based on the weighted average normal vector. The first inclination may correspond to the inclination of the weighted average normal vector.

Figure 9:
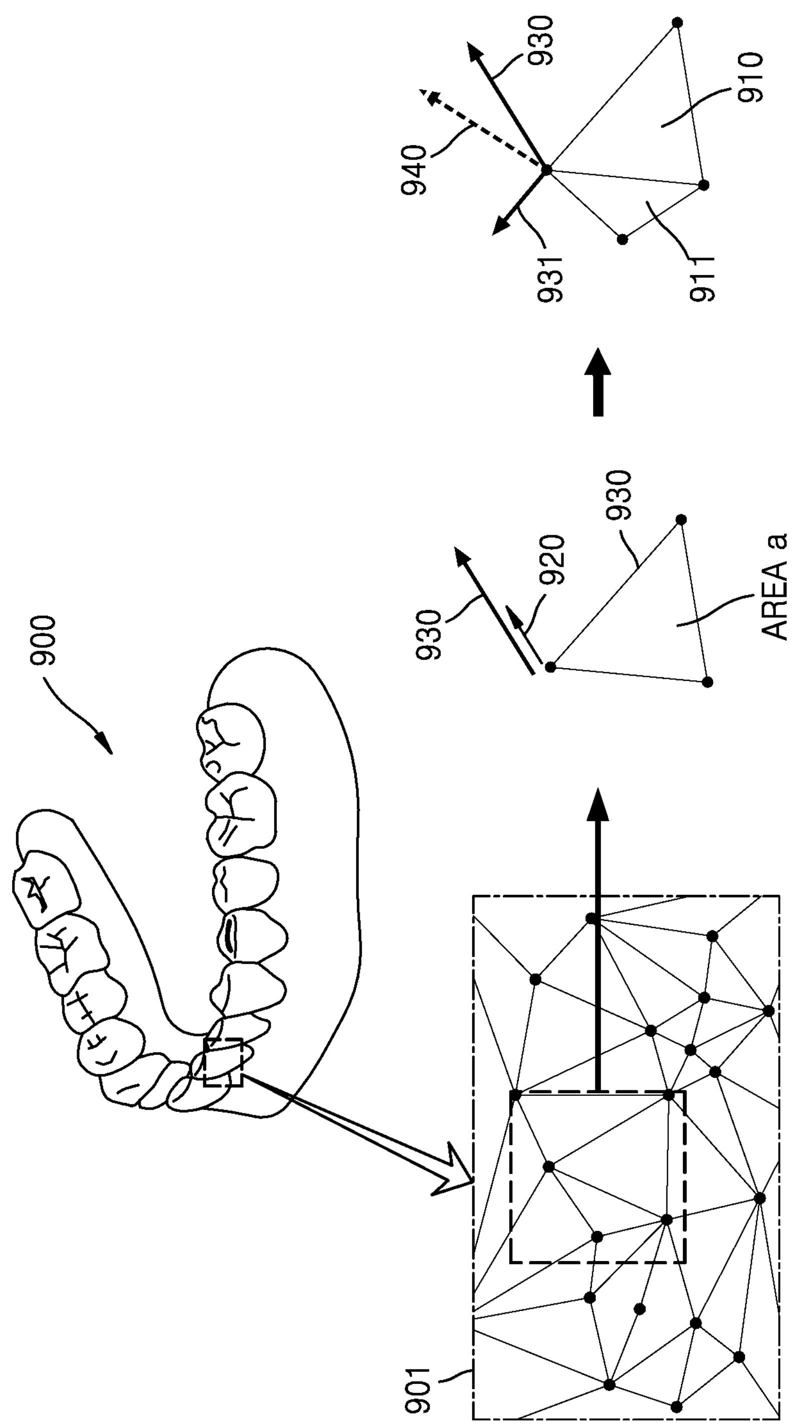
FIG. 9 is a view showing an example of a three-dimensional mesh structure of scan data according to an embodiment.

An example of a weighted average normal vector is described using two meshes with reference to FIG. 9. FIG. 9 is a view showing an example of a three-dimensional mesh structure of scan data according to an embodiment.

In FIG. 9, a partial area 901 of scan data 900 may be composed of triangular meshes generated by connecting a plurality of vertices forming a point cloud and adjacent vertices by lines. A normal vector may be defined on a surface of each of the triangular meshes. The intraoral image processing device 100 may calculate a normal vector 920 on a surface of one triangular mesh 910. The intraoral image processing device 100 may calculate an area normal vector 930 with an area a of the triangular mesh 910 applied, as a weight, to the normal vector 920. Likewise, the intraoral image processing device 100 may calculate an area normal vector 931 with an area applied, as a weight, to a normal vector of another triangular mesh 911. The intraoral image processing device 100 may calculate a weighted average normal vector 940 by averaging the area normal vectors 930 and 931 of the triangular meshes 910 and 911. The weighted average normal vector may be calculated through Equation 1 below.

$$v = \sum_{i=1}^{n} \alpha_i \hat{v}_i,\ \hat{v} = v/|v| \qquad \text{[Equation 1]}$$

In Equation 1, $\hat{v}$ denotes a weighted average unit normal vector, and $a_i$ denotes an area of each triangle forming a mesh, and $\hat{v}_i$ refers to a unit normal vector of each triangle forming a mesh.

The intraoral image processing device 100 according to an embodiment may reduce, by calculating an area of a mesh applied, as a weight, to the normal vector of the mesh, an effect on a change in density of a mesh compared with a case of considering only the normal vector of a mesh. Accordingly, a normal vector considering an area and a first inclination based thereon may be obtained.

Figure 10:
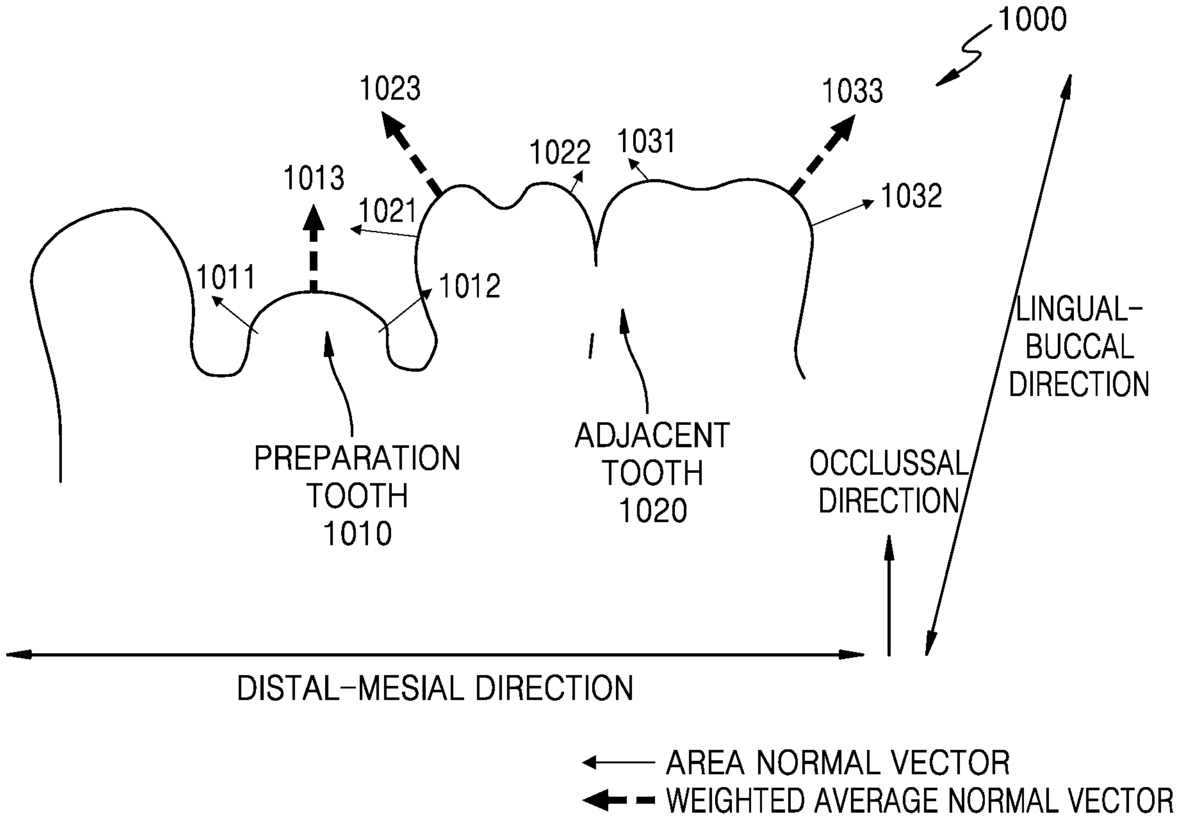
FIG. 10 is a view for explaining an operation in which an intraoral image processing device according to an embodiment obtains a first inclination of a target tooth.

An example of an operation of obtaining a first inclination from scan data 1000 including a preparation tooth 1010 and an adjacent tooth 1020 is described with reference to FIG. 10. FIG. 10 is a view for explaining an operation in which an intraoral image processing device according to an embodiment obtains a first inclination of a target tooth.

In FIG. 10, the scan data 1000 may include the preparation tooth 1010 and the adjacent tooth 1020 in which two or more teeth are arranged adjacent to each other. The preparation tooth 1010 refers to a tooth after tooth preparation and may be a tooth with at least part thereof being removed. The tooth preparation may refer to a process of cutting a corroded tooth to be covered with a prosthesis, for example, a crown and the like, or may be called "prep" for short. The adjacent tooth 1020 may be recognized as one tooth area in the scan data because two or more teeth are arranged adjacent to each other.

For example, in the preparation tooth 1010, a weighted average normal vector 1013 may face the occlusal direction. For example, in an area of the preparation tooth 1010, an area normal vector 1011 facing a distal-mesial direction (e.g., the left direction) is offset with an area normal vector 1012 facing the distal-mesial direction (e.g., the right direction), and the weighted average normal vector 1013 may face the occlusal direction according to the area normal vector facing the occlusal direction. In this case, the first inclination based on the weighted average normal vector 1013 may be parallel to an occlusal direction axis.

For example, in a first area of the adjacent tooth 1020 adjacent to the preparation tooth 1010, a weighted average normal vector 1023 may face a direction inclined the distal-mesial direction (e.g., the left direction) with respect to the occlusal direction. For example, in the first area, as the area of an area normal vector 1021 in the left direction is greater than the area of an area normal vector 1022 in the right direction, the weighted average normal vector 1023 may face a direction inclined in the left direction with respect to the occlusal direction. In this case, the first inclination based on the weighted average normal vector 1023 may have an angle inclined from the occlusal direction axis.

For example, in a second area of the adjacent tooth 1020 far from the preparation tooth 1010, a weighted average normal vector 1033 may face a direction inclined in the distal-mesial direction (e.g., the right direction) with respect to the occlusal direction. For example, in the second area, as the area of an area normal vector 1032 in the right direction is greater than the area of an area normal vector 1031 in the left direction, the weighted average normal vector 1033 may face a direction inclined in the right direction with respect to the occlusal direction. In this case, the first inclination based on the weighted average normal vector 1033 may have an angle inclined from the occlusal direction axis.

Although FIG. 10 describes, for convenience of explanation, a weighted average normal vector inclined in the distal-mesial direction, the same description may be applied to a weighted average normal vector inclined in the buccal-lingual direction.

Referring back to FIG. 8, in operation S820, the intraoral image processing device 100 may compare the first inclination of the object with the threshold inclination. For example, the intraoral image processing device 100 may obtain a final die insertion direction of an object, based on a result of comparing the first inclination of the object with the threshold inclination.

In operation S830, when the first inclination of the object is greater than the threshold inclination, the intraoral image processing device 100 may determine the threshold inclination as the final die insertion direction. For example, in FIG. 10, the first inclination based on the weighted average normal vector 1023 in the first area of the adjacent tooth 1020 may be greater than the threshold inclination. The intraoral image processing device 100 may determine a final die insertion direction of an object corresponding to the first area of the adjacent tooth 1020 as the threshold inclination, and obtain a die model having a direction based on the threshold inclination. However, the disclosure is not limited thereto, and in an embodiment, the first inclination may be less than the threshold inclination, and the intraoral image processing device 100 may operate according to operation S840. Furthermore, the same may be applied to the weighted average normal vector 1033 in the second area of the adjacent tooth 1020.

In operation S840, when the first inclination of the object is less than or equal to the threshold inclination, the intraoral image processing device 100 may determine the first inclination as the final die insertion direction. For example, in FIG. 10, as the first inclination based on the weighted average normal vector 1013 of the preparation tooth 1010 is parallel to the occlusal direction, the first inclination may be less than or equal to the threshold inclination. The intraoral image processing device 100 may determine the final die insertion direction of an object corresponding to the preparation tooth 1010 as the first inclination, and obtain a die model having a direction based on the first inclination.

Figure 11:
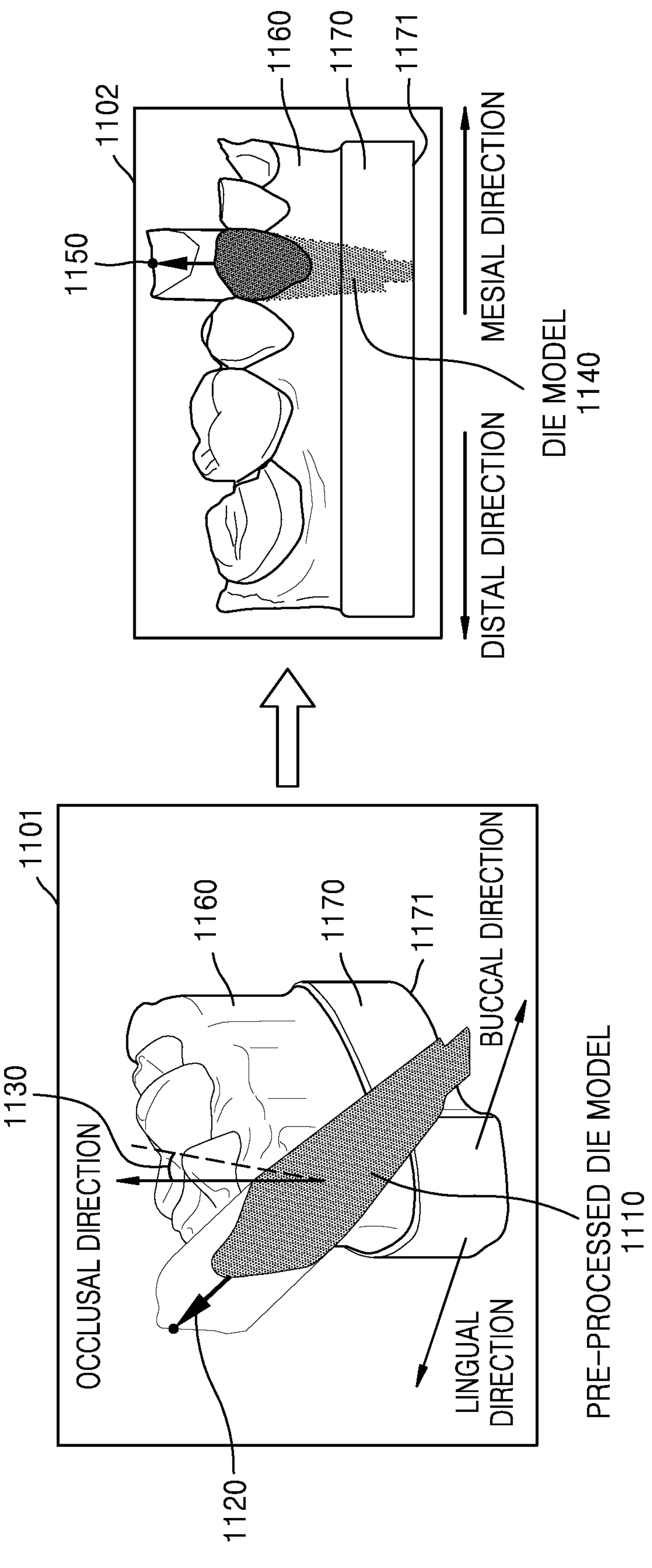
FIG. 11 is a view showing a die model obtained in an intraoral image processing device according to an embodiment.

FIG. 11 is a view showing a die model obtained in an intraoral image processing device according to an embodiment.

Referring to a diagram 1101 of FIG. 11, the intraoral image processing device 100 may obtain a pre-processed die model 1110. A die insertion direction 1120 of the pre-processed die model 1110 may be determined based on a first inclination that is greater than a threshold inclination 1130. In the disclosure, the pre-processed die model 1110 may show an example of a die model before the die insertion direction is adjusted.

For example, in an embodiment according to the disclosure, the die insertion direction 1120 of the pre-processed die model 1110 may be excessively inclined in the buccal direction, the lingual direction, the mesial direction, or the distal direction. For example, as an example, the threshold inclination based on scan data may be a value inclined within about 15 degrees in the buccal direction, not in the lingual direction, with respect to the occlusal direction axis. In this state, when the first inclination of the pre-processed die model 1110 is inclined by 20 degrees in the lingual direction with respect to the occlusal direction axis, the intraoral image processing device 100 may adjust the die insertion direction 1120 of the pretreated die model 1110 as shown in a diagram 1102 of FIG. 11. In other words, the intraoral image processing device 100 may adjust a die insertion direction 1150 based on the threshold inclination 1130.

Referring to the diagram 1102 of FIG. 11, the intraoral image processing device 100 may obtain a die model 1140 having the die insertion direction 1150 based on the threshold inclination 1130.

For example, the intraoral image processing device 100 may adjust the die insertion direction 1150 such that a lower end of a die model 1140 faces a bottom surface 1171 of a base 1170. In the disclosure, the bottom surface 1171 of the base 1170 may be parallel to the occlusal plane. For example, the intraoral image processing device 100 may adjust the die insertion direction 1150 of the die model 1140 not to face a side surface of gingiva 1160 and a side surface of the base 1170. For example, the intraoral image processing device 100 may adjust such that the die insertion direction 1150 is not inclined in the mesial direction and the distal direction with respect to the occlusal direction.

Reversely, a lower end of the pre-processed die model 1110 in the diagram 1101 of FIG. 11 may not face the bottom surface 1171 of the base 1170, may penetrate the gingiva 1160 and the base 1170 to protrude therefrom, or may be incline in the mesial direction and the distal direction.

The intraoral image processing device 100 according to an embodiment may adjust the die insertion direction based on the threshold inclination 1130 according to whether the pre-processed die model 1110 intersects the side surface of an area of the gingiva 1160 and the side surface of the base 1170.

The intraoral image processing device 100 may not display the pre-processed die model 1110 on the user interface screen.

The intraoral image processing device 100 according to an embodiment may obtain the die model 1140 corresponding to an object using scan data. The intraoral image processing device 100 may automatically calculate the die insertion direction 1150 in which the die model 1140 is formed. As an individually separable three-dimensional die model may be obtained through the intraoral image processing device 100, user convenience may be improved.

A method of calculating a threshold inclination in the intraoral image processing device 100 according to an embodiment is described below with reference to FIGS. 12 to 16

Figure 12:
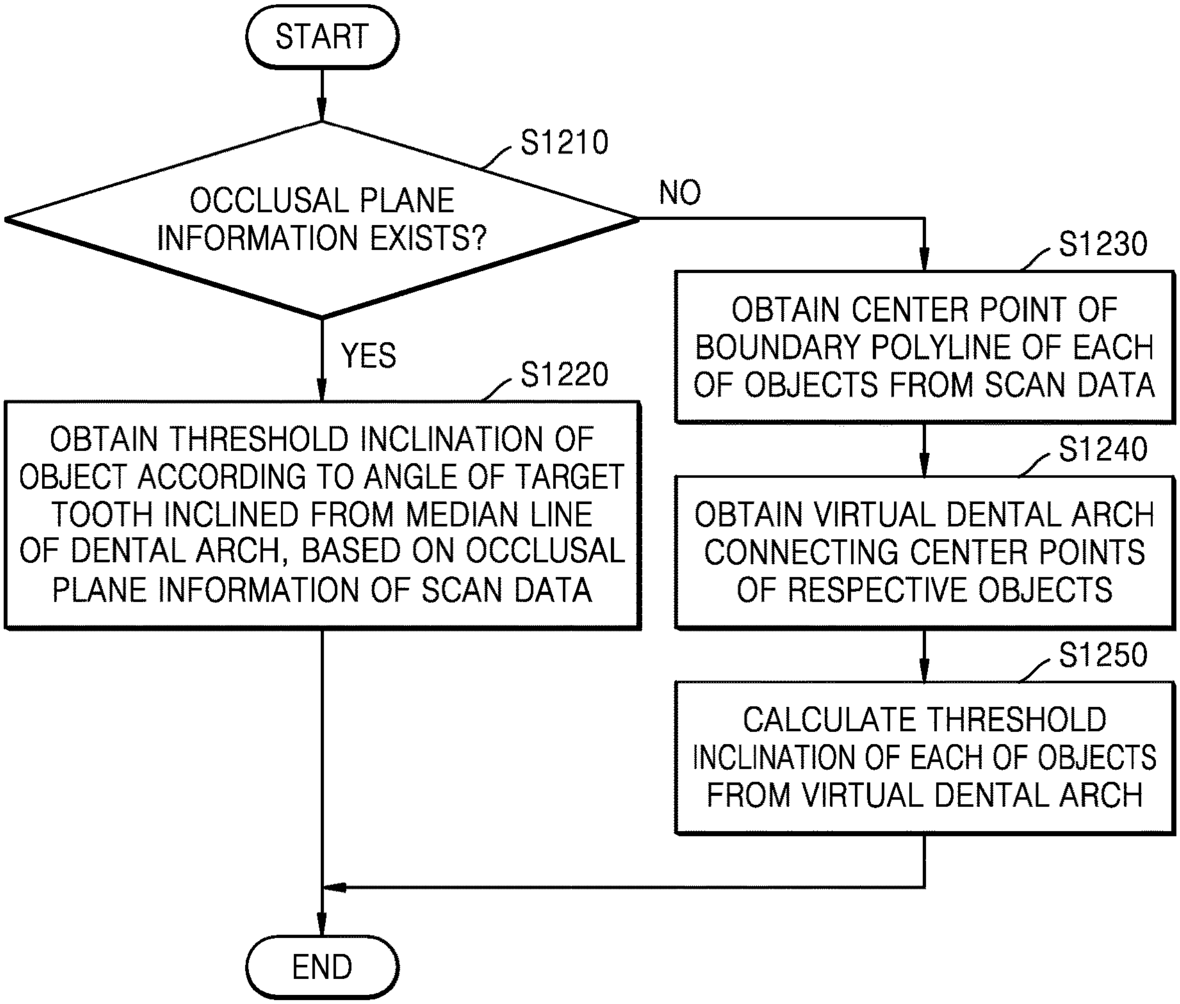
FIG. 12 is a flowchart showing a method of calculating a threshold inclination an intraoral image processing device according to an embodiment.

FIG. 12 is a flowchart showing a method of calculating a threshold inclination an intraoral image processing device according to an embodiment.

Referring to FIG. 12, in operation S1210, the intraoral image processing device 100 may identify whether occlusal plane information of scan data exists.

In operation S1220, when the occlusal plane information of scan data is determined to exist, the intraoral image processing device 100 may obtain a threshold inclination according to an angle of an object inclined from a median line of a dental arch, based on the occlusal plane information of the scan data.

In operation S1230, when the occlusal plane information of scan data is determined not to exist, the intraoral image processing device 100 may obtain a center point of a boundary polyline of each of objects from the scan data.

For example, the intraoral image processing device 100 may perform any one operation of calculating an average of vertex coordinates forming a boundary polyline of each object, calculating a center coordinate of a bounding box including each object, and calculating a weighted average with the length of each of line segments forming the boundary polyline of each object applied, as a weight, to the center coordinate of each of the line segments. The method of calculating a threshold inclination an intraoral image processing device according to an embodiment will be described in detail with reference to FIGS. 16A, 16B, and 16C.

In operation S1240, the intraoral image processing device 100 may obtain a virtual dental arch connecting the center points of respective objects.

In operation S1250, the intraoral image processing device 100 may calculate the threshold inclination of each of the objects from the virtual dental arch. For example, the intraoral image processing device 100 may calculate a normal vector that is perpendicular to each virtual dental arch as a threshold inclination, but the disclosure is not limited thereto.

Figure 13:
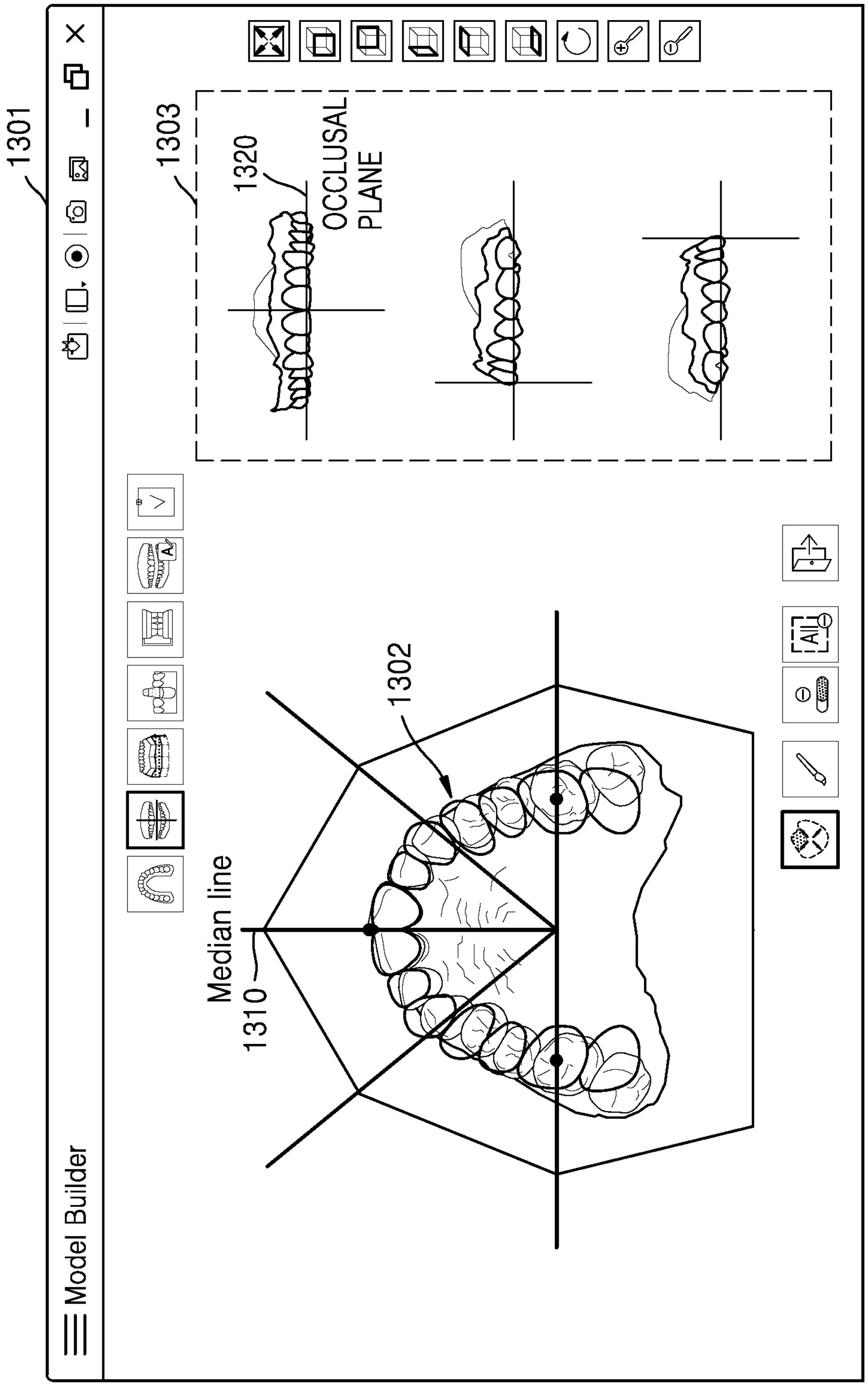
FIG. 13 is a view for explaining an operation of calculating a threshold inclination when occlusal plane information exists, in an intraoral image processing device according to an embodiment.

FIG. 13 is a view for explaining an operation of calculating a threshold inclination when occlusal plane information exists, in an intraoral image processing device according to an embodiment.

Referring to FIG. 13, the intraoral image processing device 100 may include occlusal plane information 1303 of scan data 1302. The intraoral image processing device 100 may display the scan data 1302 including the occlusal plane information 1303 on a user interface screen 1301. In the scan data 1302 including the occlusal plane information 1303, an occlusal surface of an object may be located on an occlusal plane 1320, and the center of the object and a median line 1310 of a dental arch may match each other. When the scan data 1302 includes the occlusal plane information 1303, an occlusal direction axis is determined so that a preset threshold inclination may be obtained according to the position of a tooth.

The intraoral image processing device 100 according to an embodiment may obtain a threshold inclination with respect to any one of the buccal direction, the lingual direction, the mesial direction, and the distal direction according to an angle of the object inclined from the median line 1310 along the dental arch.

For example, when an object is inclined by 10 degrees from the median line 1310 along the dental arch, the object corresponds to the anterior tooth, and thus, the threshold inclination may include any one of a certain inclination (e.g., 15 degrees) in the buccal direction, 0 degrees in the lingual direction, 0 degrees in the distal direction, and 0 degrees in the mesial direction.

For example, when an object is inclined by 50 degrees from the median line 1310 along the dental arch, the object corresponds to the posterior tooth, and thus, the threshold inclination may include any one of a certain inclination (e.g., 5 degrees) in the buccal direction, 0 degrees in the lingual direction, 0 degrees in the distal direction, and 0 degrees in the mesial direction.

In the disclosure, the angle of an object inclined along a dental arch and the angle of the threshold inclination are examples for convenience of explanation, and are not limited to the values described above.

Figure 14:
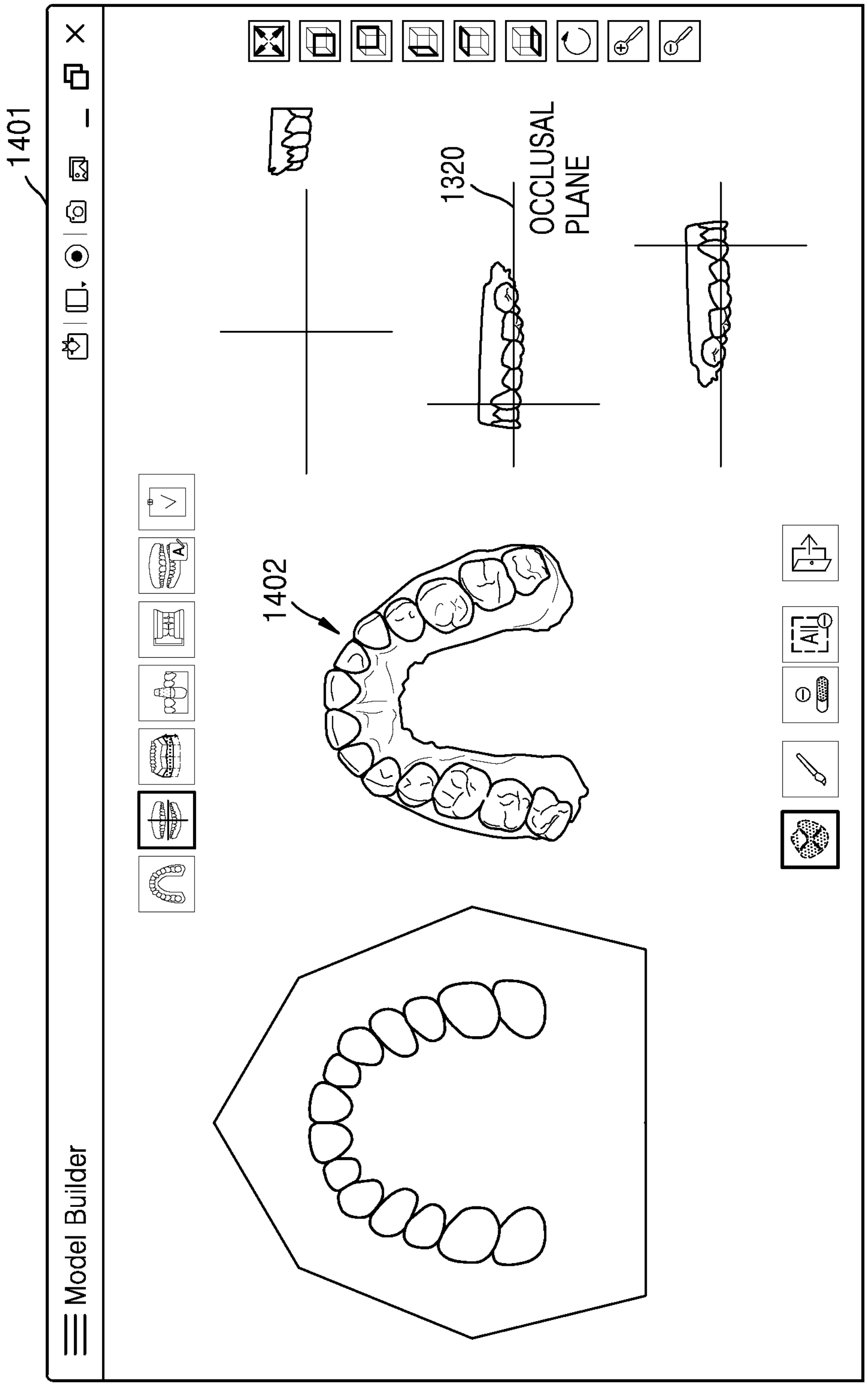
FIG. 14 is a view showing a user interface when no occlusal plane information exists, in an intraoral image processing device according to an embodiment.
Figure 15:
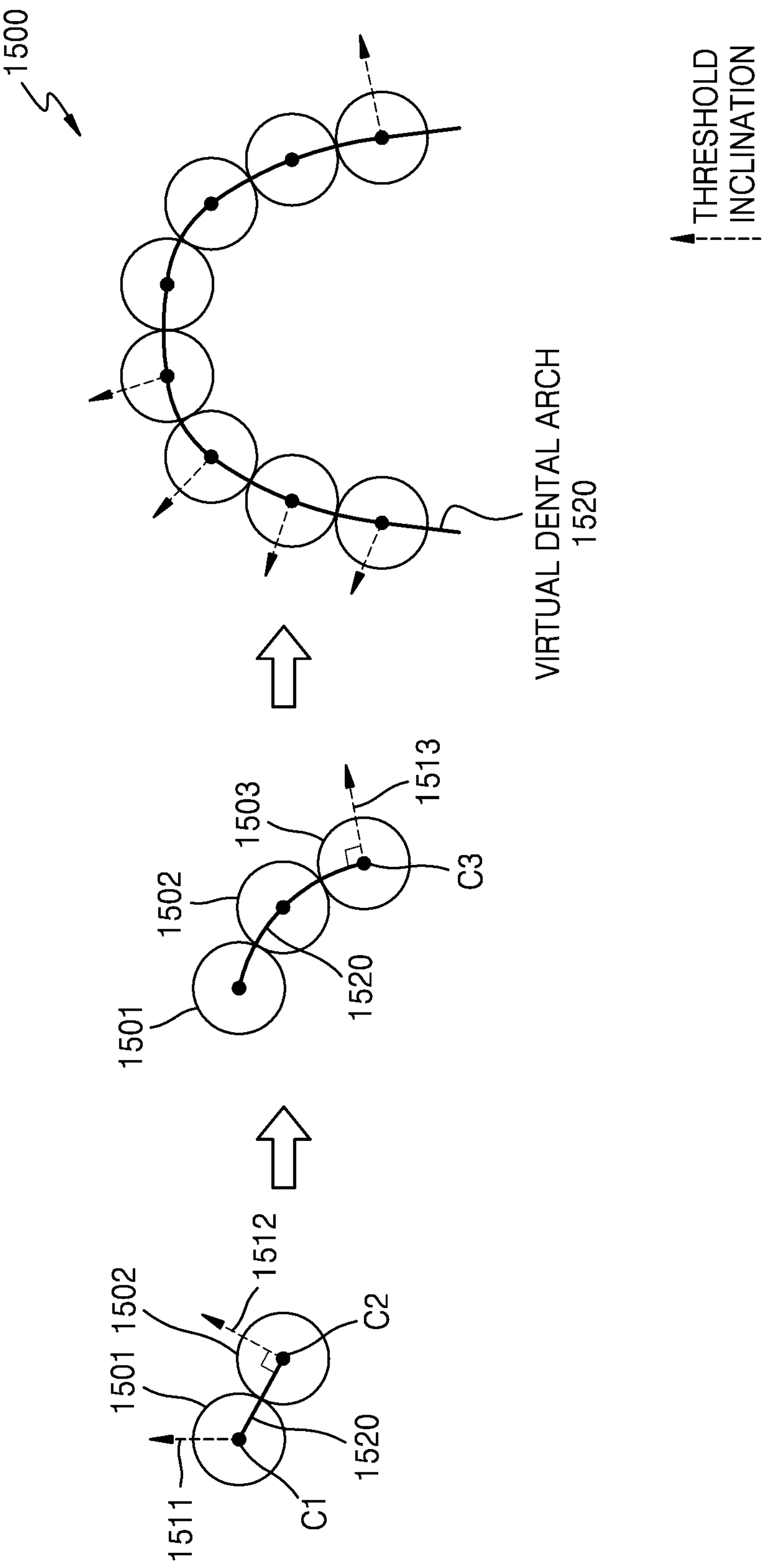
FIG. 15 is a view for explaining an operation of calculating a threshold inclination when no occlusal plane information exists, in an intraoral image processing device according to an embodiment.

Next, a case in which the occlusal plane information of scan data does not exist is described with reference to FIGS. 14 and 15. FIG. 14 is a view showing a user interface when no occlusal plane information exists, in an intraoral image processing device according to an embodiment. FIG. 15 is a view for explaining an operation of calculating a threshold inclination when no occlusal plane information exists, in an intraoral image processing device according to an embodiment.

Referring to FIG. 14, the intraoral image processing device 100 may not include occlusal plane information of scan data 1402. The intraoral image processing device 100 may display the scan data 1402 that does not include occlusal plane information on a user interface screen 1401. The intraoral image processing device 100 may obtain at least the position of an occlusal surface of the scan data 1402 (e.g., tooth's upper and lower jaws information) based on a user input to provide the occlusal plane information of the scan data 1402. When the intraoral image processing device 100 includes information about the position of an occlusal surface, instead of information about an occlusal plane, the threshold inclination may be calculated through a virtual dental arch. The intraoral image processing device 100 may output an error message (not shown) (e.g., "Please input occlusal plane information.") to obtain occlusal plane informationthrough the user interface screen 1401.

Referring to FIG. 15, the intraoral image processing device 100 may obtain a virtual dental arch 1520 connecting the center points of respective objects. The intraoral image processing device 100 may calculate the threshold inclination of each of the objects from the virtual dental arch 1520.

First, the intraoral image processing device 100 may obtain a center point C1 of a first tooth area 1501 based on first object. The intraoral image processing device 100 may obtain a center point C2 of a second tooth area 1502 based on a second object. The virtual dental arch 1520 may be formed by connecting the center point C1 of the first tooth area 1501 to the center point C2 of the second tooth area 1502.

Next, the intraoral image processing device 100 may obtain a center point C3 of a third tooth area 1503 based on a third object, and the virtual dental arch 1520 may be formed by connecting the center point C1 and the center point C2 to the center point C3.

The intraoral image processing device 100 may calculate threshold inclinations 1511, 1512, and 1513 of the respective objects by forming the virtual dental arch 1520. The threshold inclinations 1511, 1512, and 1513 of the respective objects may have inclinations of normal vectors perpendicular to the virtual dental arch 1520.

Figure 16A:
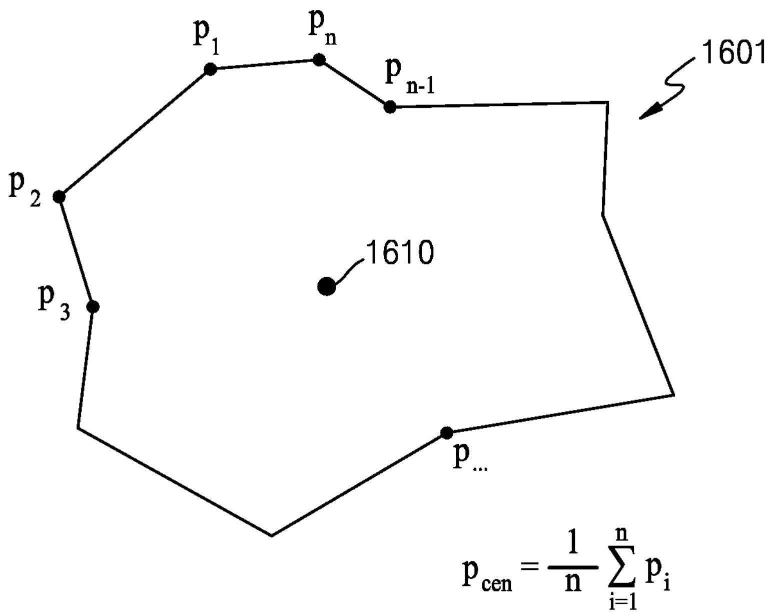
FIGS. 16A, 16B, and 16C are views for explaining an operation of obtaining a center point of a boundary of a tooth area from scan data in an intraoral image processing device according to an embodiment.
Figure 16B:
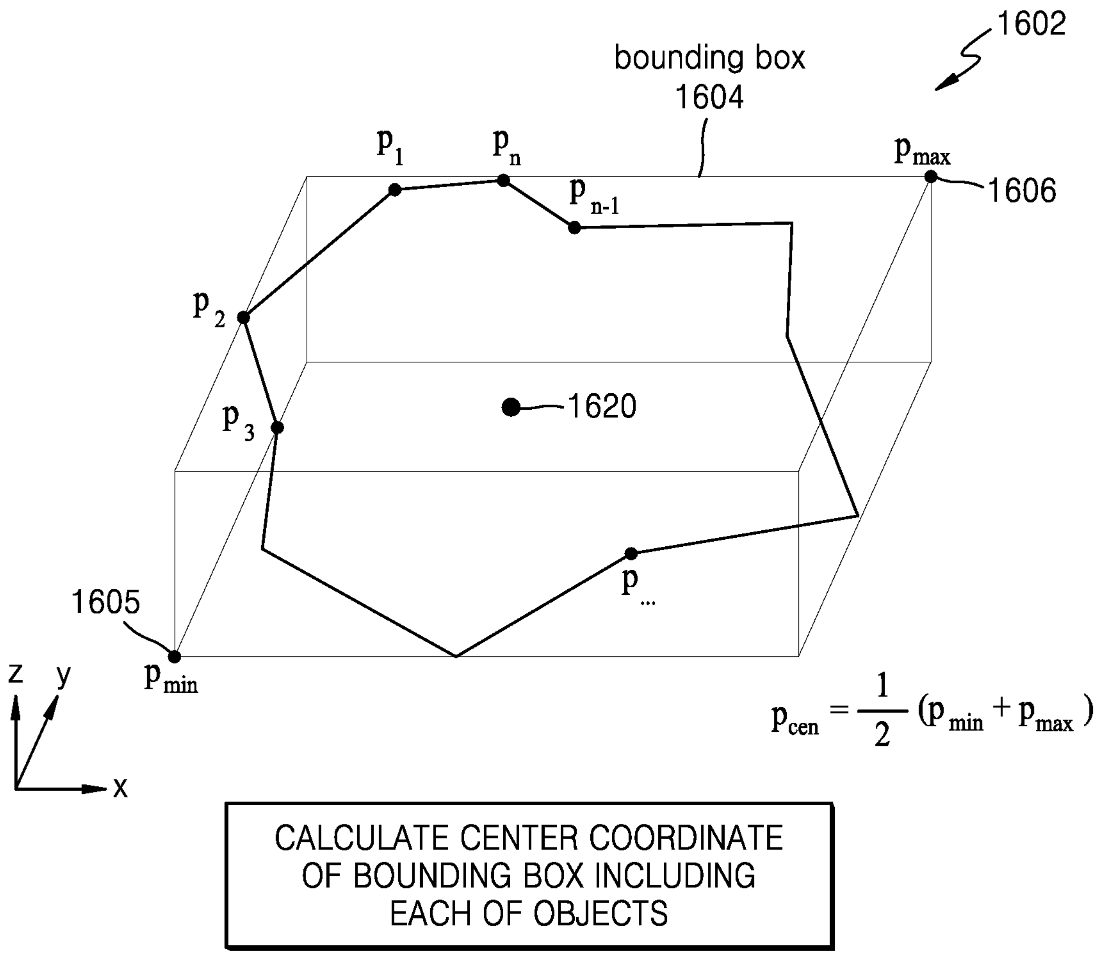
Figure 16C:
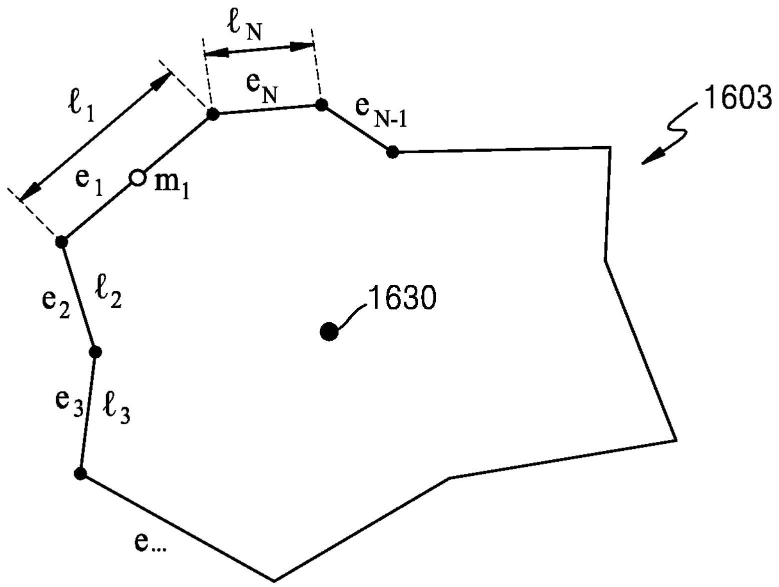

Next, a method of obtaining a boundary center point of a tooth area is described with reference to FIGS. 16A to 16C. FIGS. 16A, 16B, and 16C is a view for explaining an operation of obtaining a center point of a boundary of a tooth area from scan data in an intraoral image processing device according to an embodiment.

In FIGS. 16A to 16C, the intraoral image processing device 100 may obtain a center point of a boundary polyline of each of objects from scan data. The intraoral image processing device 100 may include coordinates information of vertexes $p_1, p_2, p_3, \ldots, p_n$ of a boundary of a tooth area recorded in the form of a point cloud in the scan data. Furthermore, the intraoral image processing device 100 may include connection relationship information of each of the vertexes $p_1, p_2, p_3, \ldots, p_n$ of a boundary of a tooth area recorded in scan data.

In FIG. 16A, the intraoral image processing device 100 may calculate an average of the vertex coordinates forming a boundary polyline of each of objects. For example, the intraoral image processing device 100 may calculate the average of the vertex coordinates $p_1, p_2, p_3, \ldots, p_n$ of the boundary of a tooth area 1601 of an object. The intraoral image processing device 100 may obtain a center point 1610 of the tooth area 1601. In this case, Equation 2 may be employed.

$$p_{cen} = \frac{1}{n}\sum_{i=1}^{n} p_i \qquad \text{[Equation 2]}$$

In Equation 2, $p_{cen}$ is the center point 1610 of the tooth area 1601 according to an embodiment, n is the number of vertex coordinates, and $p_i$ is a point coordinate.

In FIG. 16B, the intraoral image processing device 100 may calculate the center coordinate of a bounding box including each of the objects. For example, the intraoral image processing device 100 may obtain a bounding box 1604 including a tooth area 1602. The intraoral image processing device 100 may calculate a center coordinate 1620 of the bounding box 1604 through a minimum coordinate 1605 and a maximum coordinate 1606 of the bounding box 1604. In the disclosure, an x-axis denotes the buccal direction of a tooth, a y-axis denotes the occlusal direction, and a z-axis denotes the mesial-distal direction, but the disclosure is not limited thereto. The intraoral image processing device 100 may obtain a center point 1620 of the tooth area 1602. In this case, Equation 3 may be employed.

$$p_{cen} = \frac{1}{2}(p_{min} + p_{max}) \qquad \text{[Equation 3]}$$

In Equation 3, $p_{cen}$ denotes the center point 1620 of the tooth area 1602 according to an embodiment, $p_{min}$ denotes the minimum coordinate 1605 of the bounding box 1604, and $p_{max}$ denotes the maximum coordinate 1606 of the bounding box 1604.

In FIG. 16C, the intraoral image processing device 100 may calculate a weighted average with the length of each of line segments forming the boundary polyline of each object applied, as a weight, to the center coordinate of each of the line segments with the length of each of line segments. For example, the intraoral image processing device 100 may include coordinates and length l1, l2, l3, . . . , and ln of line segments e1, e2, e3, . . . , and en connecting vertices of a boundary of a tooth area 1603 including an object. Furthermore, the intraoral image processing device 100 may include center coordinates m1, m2, m3, . . . , and mn of the respective line segments forming the tooth area 1603. The intraoral image processing device 100 may calculate a length weighted average with the lengths l1, l2, l3, . . . , and ln of the line segments applied, as a weight, to the center coordinates m1, m2, m3, . . . , and mn of the respective line segments forming the tooth area 1603. The intraoral image processing device 100 may obtain a center point 1630 of the tooth area 1603. In this case, Equation 4 may be employed.

$$p_{cen} = \frac{1}{L}\sum_{i=1}^{N}\ell_i m_i,\ L = \sum_{i=1}^{N}\ell_i,\ m = \text{midpoint of a segment } e_i \quad \text{[Equation 4]}$$

In Equation 4, $p_{cen}$ denotes the center point 1630 of the tooth area 1603 according to an embodiment, $m_i$ denotes the center coordinate of a line segment $e_i$, $l_i$ denotes the length of the line segment $e_i$, and L denotes the sum of the length of line segments of the tooth area 1603.

The intraoral image processing method according to an embodiment of the disclosure may be embodied as program instructions executable by various computer devices, and recorded on a computer-readable medium. Furthermore, an embodiment of the disclosure may be implemented in a computer-readable recording medium having recorded thereon one or more programs including instructions for executing the intraoral image processing method.

The computer-readable medium may include program instructions, data files, data structures, or the like separately or in combinations. Examples of the computer-readable recording medium include magnetic media such as hard disks, floppy disks, or magnetic tapes, optical media such as compact disc ROMs (CD-ROMs) or digital video discs (DVDs), magneto-optical media such as floptical disks, and hardware devices such as ROM, RAM, and flash memory, which are specially configured to store and execute program instructions.

Here, the machine-readable storage medium may be provided in the form of a non-transitory storage medium. Here, the term "non-transitory" merely means a tangible storage medium. Furthermore, the "non-transitory storage medium" may include a buffer in which data is temporarily stored.

According to an embodiment of the present disclosure, the methods according to various embodiments disclosed herein may be included in a computer program product and then provided. The computer program product may be distributed in the form of a machine-readable storage medium (e.g., a CD-ROM). Alternatively, the computer program product may be distributed online (e.g., downloaded or uploaded) through an application store (e.g., Play Store™) or directly between two user devices (e.g., smart phones) In detail, there may be an implemented computer program product including a recording medium having recorded thereon a program for performing the intraoral image processing method according to an embodiment of the present disclosure Although embodiments have been described above in detail, the scope of the present disclosure is not limited thereto, and various modifications and alterations by those skill in the art using the basic concept of the present disclosure defined in the following claims also fall within the scope of the present disclosure.

The invention claimed is:

1. An intraoral image processing method comprising:
obtaining an intraoral image by scanning an object;
determining a die insertion direction corresponding to a first inclination of the object based on mesh information representing a shape of a surface included in the intraoral image;
in response to the first inclination of the object being greater than a threshold inclination, adjusting the die insertion direction to be set within the threshold inclination; and
obtaining a die model set in the die insertion direction.

2. The intraoral image processing method of claim 1, wherein
the determining of the die insertion direction comprises adjusting a lower end of the die model to face a bottom of a base, wherein the base indicates a plate of a tooth model and the die model is detachable to the base of the tooth model.

3. The intraoral image processing method of claim 1, wherein
the determining of the die insertion direction comprises adjusting the die insertion direction not to face a side surface of a gingiva and a side surface of a base, wherein the base indicates a plate of a tooth model and the die model is detachable to the base of the tooth model.

4. The intraoral image processing method of claim 1, wherein
the determining of the die insertion direction comprises adjusting the die insertion direction not to be inclined in a mesial direction and a distal direction with respect to an occlusal direction.

5. The intraoral image processing method of claim 1, wherein
the adjusting of the final die insertion direction comprises:
in response to the first inclination of the object being greater than the threshold inclination, determining the threshold inclination as the final die insertion direction; and
in response to the first inclination of the object being less than or equal to the threshold inclination, determining the first inclination as the final die insertion direction.

6. The intraoral image processing method of claim 1, wherein
the threshold inclination comprises an angle in any one of a buccal direction, a lingual direction, a mesial direction, and a distal direction with respect to an occlusal direction.

7. The intraoral image processing method of claim 1, wherein
the obtaining of the first inclination of the object comprises:

obtaining a weighted average normal vector with an area applied, as a weight, to a normal vector based on the mesh information included in the intraoral image of the object; and obtaining the first inclination of the object based on the weighted average normal vector.

8. An intraoral image processing device comprising:

a memory to store one or more instructions; and a processor, wherein the processor is configured to, by executing the one or more instructions stored in the memory:

obtain an intraoral image by scanning an object;

determine a die insertion direction corresponding to a first inclination of the object based on mesh information representing a shape of a surface included in the intraoral image;

in response to the first inclination of the object being greater than a threshold inclination, adjust the die insertion direction to be set within the threshold inclination; and obtain a die model set in the die insertion direction.

9. The intraoral image processing device of claim 8, wherein the processor is further configured to, by executing the one or more instructions stored in the memory, adjust a lower end of the die model to face a bottom of a base, wherein the base indicates a plate of a tooth model and the die model is detachable to the base of the tooth model.

10. The intraoral image processing device of claim 8, wherein the processor is further configured to, by executing the one or more instructions stored in the memory, adjust the die insertion direction not to face a side surface of a gingiva and a side surface of a base, wherein the base indicates a plate of a tooth model and the die model is detachable to the base of the tooth model.

11. The intraoral image processing device of claim 8, wherein the processor is further configured to, by executing the one or more instructions stored in the memory, adjust the die insertion direction not to be inclined in a mesial direction and a distal direction with respect to an occlusal direction.

12. The intraoral image processing device of claim 8, wherein the processor is further configured to, by executing the one or more instructions stored in the memory:

in response to the first inclination of the object being greater than the threshold inclination, determine the threshold inclination as the final die insertion direction; and in response to the first inclination of the object being less than or equal to the threshold inclination, determine the first inclination as the final die insertion direction.

13. The intraoral image processing device of claim 8, wherein the processor is further configured to, by executing the one or more instructions stored in the memory:

obtain a weighted average normal vector with an area applied, as a weight, to a normal vector based on the mesh information included in the intraoral image of the object; and obtain the first inclination of the object based on the weighted average normal vector.

* * * * *